(12) United States Patent
Fiedler et al.

(10) Patent No.: US 7,601,803 B1
(45) Date of Patent: Oct. 13, 2009

(54) FABRICATION OF BETA-PLEATED SHEET PROTEINS WITH SPECIFIC BINDING PROPERTIES

(75) Inventors: Ulrike Fiedler, Halle (DE); Rainer Rudolph, Halle (DE); Gerald Boehm, Wuerzburg (DE); Carola Reimann, Halle (DE)

(73) Assignee: Scil Proteins GmbH, Halle (DE)

( * ) Notice: Subject to any disclaimer, the term of this patent is extended or adjusted under 35 U.S.C. 154(b) by 584 days.

(21) Appl. No.: 10/030,605

(22) PCT Filed: Jul. 13, 2000

(86) PCT No.: PCT/EP00/06698

§ 371 (c)(1),
(2), (4) Date: May 31, 2002

(87) PCT Pub. No.: WO01/04144

PCT Pub. Date: Jan. 18, 2001

(30) Foreign Application Priority Data

Jul. 13, 1999 (DE) .................................. 199 32 688

(51) Int. Cl.
*A61K 38/16* (2006.01)
(52) U.S. Cl. ............................. 530/350; 514/2; 514/12
(58) Field of Classification Search .................. 500/324; 530/350
See application file for complete search history.

(56) References Cited

U.S. PATENT DOCUMENTS 6,673,901 B2 * 1/2004 Koide .......................... 530/380

FOREIGN PATENT DOCUMENTS

| FR | 2761688 A | 10/1998 |
|---|---|---|
| WO | WO9716556 A1 | 5/1997 |
| WO | WO 98/44121 | 10/1998 |
| WO | WO9854312 A1 | 12/1998 |
| WO | WO9916873 A1 | 4/1999 |

OTHER PUBLICATIONS

Beste et al. Small antibody-like proteins with prescribed ligand specificities derived from the lipocalin fold. PNAS 1999 96:1898-1903.*
Chirgadze et al. Structure of the Bovine Eye Lens gamma-IIb-Crystallin at 1.95 A., Acta Cryst 1996 D52 712-721.*
den Dunnen et al. Database PIR__79, Accession No. B24060; J. Mol. Biol., 189,37-46,1986.*
den Dunnen et al Database PIR__79, Accession No. A24060; Gene, 38, 197-204, 1985.*
Graw et al. al Database UniProt, Accession No. P04344; Gene,136, 145-156, 1993.*
Guo et al. Protein tolerance to random amino acid change, PNAS, 101(25), 9205-9210, 2004.*
Beste et al Proc. Nartl. Acad. Sci., USA, 96, 1898-1903, 1999.*
International Search Report for PCT/EP00/06698; pp. 1-3.

Campion, Stephen R., et al., "Biochemical Properties of Site-Directed Mutants of Human Epidermal Growth Factor: Importance of Solvent-Exposed Hydrophobic Residues of the Amiono-Terminal Domain in Receptor Binding," *Biochemistry*, 29, (No. 42):9988-9993 (1990).
Slingsby, Christine; Clout, Naomi J., (XP-000971615) "Structure of the Crystallins," *Eye* (London),13:395-402 ( May 6, 1999).
Saviranta, Petri et al., "Engineering the steroid-specificity of an anti-17β-estradiol Fab by random mutagenesis and competitive phage panning," *Protein Engineering*, 11:143-152 ( Feb. 6, 1998).
Exley, Donald; Woodhams, Barry, "The Specificity of Antisera Raised by Oestradiol-17β -3-Hemisuccinyl-Bovine Serum Albumin," *Steroids*, 27 ( No. 6):813-820 (1976).
Jaenicke, Rainer, "Stability and folding of domain proteins," *Progression Biophysics & Molecular Biology*,71 ( No. 2):155-241 (1999).
Jenkins, John et al., "Structure and Evolution of Parallel β -Helix Proteins," *J. of Structural Biology*, 122:236-246 (1998).
Nord, Karin et al., "Binding Proteins Selected from Combinatorial Libraries of an α-helical bacterial receptor domain," *Nature Biotechnology*, 15:772-777 (1997).
Palme, Stefan et al., "Mutational analysis of hydrophobic domain interactions in γB-crytallin from bovine eye lens," *Protein Science*, 6:1529-1536 (1997).
European Patent Office Exaination Report dated Apr. 2, 2007 for Euopean Patent Application No. 06118519.5.
Abedi et al, "Green fluorescent protein as a scaffold for intracellular presentation of peptide", (1998).
Koide et al, "The Fibronectin Type IIIDomain as a Scaffold for Novel Binding Proteins", J. Mol. Biol, vol. 284 pp. 1141-1151 (1998).
McConnell et al., Tendamistat as a Scaffold for Conformationally Contrained Phage Peptide Libraries, J. Mol. Biol., vol. 250 pp. 460-470 (1995).
Mueller et al., "Grafting of a High-Affinity Zn(II)-Binding Site on the β-Barrel of Retional-Binding Protein Results in Enhanced Folding Stability and Enables Simplified Purification," Biochemistry, vol. 33, pp. 14126-14135 (1994).
Nygren et al., "Scaffolds for enginerring novel binding sites in proteins", pp. 463-469.
Palme et al., "Mutational analysis of hydrophobic domain interactions in yB-crystallin from bovin eye lens", Protein Science, vol. 6, pp. 1529-1536 (1997).
Saviranta et al., "Engeineering the steriod-specificity of an anti-17B-estradiol Fab by random mutagenesis and competitive phage panning", pp. 143-152.
Smith et al., "Small Binding Proteins Selected from a Conbinatorial Repertoire of Knottins Displayed on Phage", J. Mol. Biol., vol. 277, pp. 317-332 (1998).
European Office Action from the European Patent Office dated Oct. 7, 2004.
Xia et al., "Crystal structure of the receptor-binding domain of adenovirus type 5 fiber protein at 1.7 A resolution", *Structure*, 2:1259-1270, Dec. 15, 1994.
Voet & Voet, *Biochemistry* Chapter 7. Three-Dimensional Structures of Proteins, 1990.

* cited by examiner

*Primary Examiner*—Michael Borin
(74) *Attorney, Agent, or Firm*—Jenkins, Wilson, Taylor & Hunt, P.A.

(57) ABSTRACT

The present invention describes novel beta-sheet proteins having specific binding properties and catalytic properties and also methods for preparing these proteins.

5 Claims, 8 Drawing Sheets

Fig. 1

GCLIE1B: Biotin- CGCGCGCGTCTCACAAAGATACATGCCATGACTCGCGGCCCAGCC
GCLIE2P: P- CCCCATGGCCGGCTGGGCCGCGAGTCATGGCATGTATCTTTGTGAGACGCGCGCG
GCLI3P: P- GGCCATGGGGNNKATCNNKTTTNNKGAGGACCGGGG
GCLIB4P: P- GTGGCCCTGGAAGCCCCGGTCCTC
GCLI5P: P- CTTCCAGGGCCACNNKTACNNKTGCNNKAGCGACTGCCCCAACC
GCLI6P: P- TGCAGCCCTATTTCAGCCGC
GCLIB7P: P- GATGGAGTTACAGCGGCTGAAATAGGGCTGCAGGTTGGGGCAGTCGC
GCLI8P: p- TGTAACTCCATCNNKGTGNNKAGCGGCTGCTGGATGCTGTATGAG
GCLIE9P: P- CGCCCCAACTACCAGGGTCACCAGTACTTCCTGCGGC
GCLIE10: GCCGCAGGAAGTACTGGTGACCCTGGTAGTTGGGGCGCTCATACAGCATC
GCLIA11B: Biotin- CCATCAGCCCCATCAGCGAACTTTGCCGCAGGAAGTACTGG P: Phosphate, N: A/C/G/T, K: T/G

Fig. 2

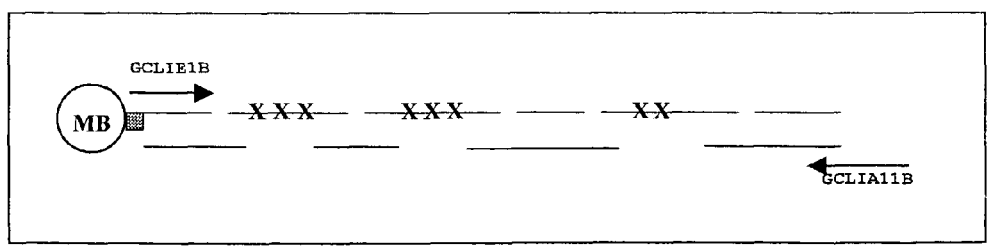

GCFORNOT: 5' GAGTCATTCTGCGGCCGCATAAAAATCCATCACCCGTCTTAAAGAACC 3'

GCBACKSfiBst: 5' GCGGCCCAGCCGGCCGCTGCTGGATGCTGTATGAGCGCCCCAACTACCAGGGTCACCAG 3' amber stop

Fig. 7

Mu 12A:
<u>GGCCCAGCCGGCC</u>ATGGGGAGGATCAAGTTTAAAGAGGACCGGGGCTTCCAGGGCCA
CTATTACAGTTGCAATAGCGACTGCCCCAACCTGCAGCCCTATTTCAGCCGCTGTAACT
CCATCAGGGTGCTGAGCGGCTGCTGGATGCTGTATGAGCGCCCCAACTACCAG<u>GGTCA
CC</u>

WT:
<u>GGCCCAGCCGGCC</u>ATGGGGAAGATCACTTTTTACGAGGACCGGGGCTTCCAGGGCCA
CTGCTACGAGTGCAGCAGCGACTGCCCCAACCTGCAGCCCTATTTCAGCCGCTGTAAC
TCCATCCGCGTGGACAGCGGCTGCTGGATGCTGTATGAGCGCCCCAACTACCAGGGC
CACC

Fig. 8

Mu 12A:
*AAQPA*MGRIKFKEDRGFQGHYY<u>SCN</u>SDCPNLQPYFSRCNSIRVL<u>S</u>GCWMLYERPNYQGH
QYFLRRGDYPDYQQWMGFNDSIRSCRLIPQHTGTFRMRIYERDDFRGQMSEITDDCPSLQ
DRFHLTEVHSLNVLEGSWVLYEMPSYRGRQYLLRPGEYRRYLDWGAMNAKVGSLRRVMD
FY*AAAGAPVPYPDPLEPRAA*

WT:
*AAQPA*MGKITFYEDRGFQGHCYECSSDCPNLQPYFSRCNSIRVDSGCWMLYERPNYQGH
QYFLRRGDYPDYQQWMGFNDSIRSCRLIPQHTGTFRMRIYERDDFRGQMSEITDDCPSLQ
DRFHLTEVHSLNVLEGSWVLYEMPSYRGRQYLLRPGEYRRYLDWGAMNAKVGSLRRVMD
FY*AAAGAPVPYPDPLEPRAA*

Fig. 9

GC 20bbackWT:   5' GGGAATTCCATATGGGGAAGATCACTTTTTACG 3'
GC 20bback12A:  5' GGGAATTCCATATGGGGAGGATCAAGTTTAAAG 3'
GC for 20b:     5' CGCGGATCCGAATAAAAATCCATCACCCG 3'

Fig. 10

Mu 12A-HIS:
MGRIKFKEDRGFQGHYYSCNSDCPNLQPYFSRCNSIRVLSGCWMLYERPNYQGHQYFLR
RGDYPDYQQWMGFNDSIRSCRLIPQHTGTFRMRIYERDDFRGQMSEITDDCPSLQDRFHL
TEVHSLNVLEGSWVLYEMPSYRGRQYLLRPGEYRRYLDWGAMNAKVGSLRRVMDFY*SDP*
*NSSSVDKLAAALEHHHHHH*

WT-HIS:
MGKITFYEDRGFQGHCYECSSDCPNLQPYFSRCNSIRVDSGCWMLYERPNYQGHQYFLR
RGDYPDYQQWMGFNDSIRSCRLIPQHTGTFRMRIYERDDFRGQMSEITDDCPSLQDRFHL
TEVHSLNVLEGSWVLYEMPSYRGRQYLLRPGEYRRYLDWGAMNAKVGSLRRVMDFY*SDP*
*NSSSVDKLAAALEHHHHHH*

Fig. 11

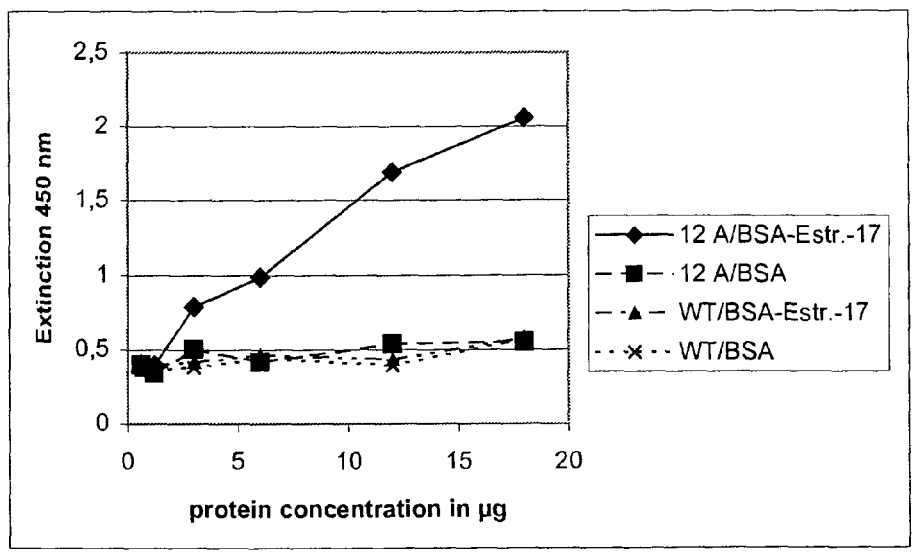

Fig. 12
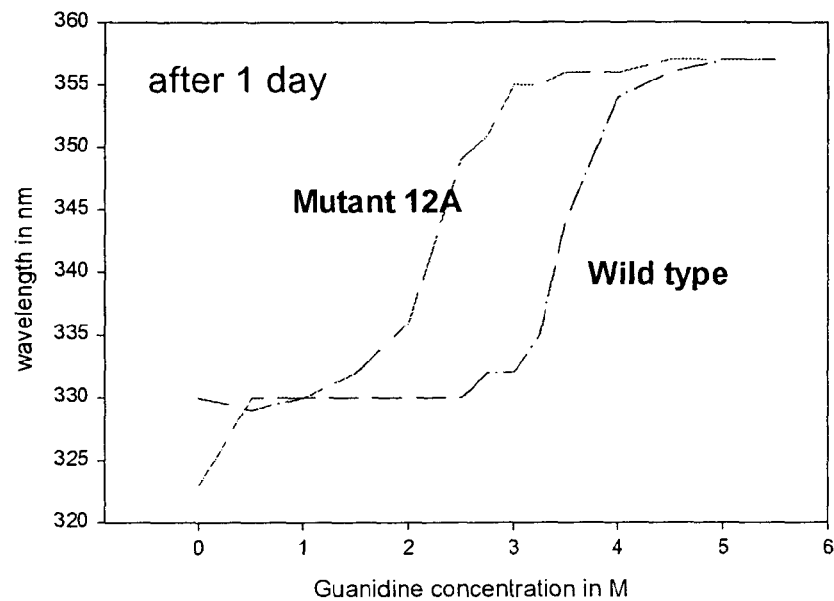
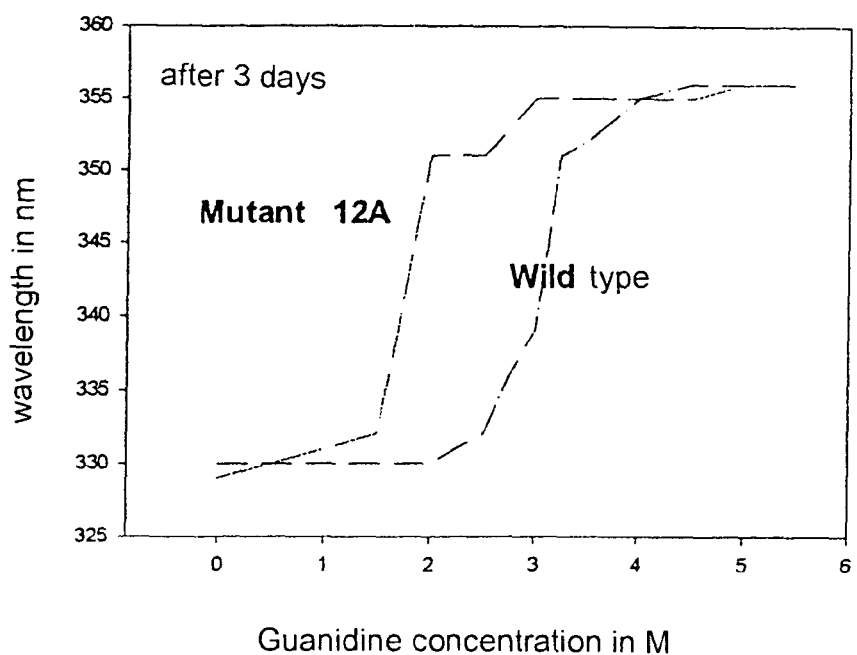

FABRICATION OF BETA-PLEATED SHEET PROTEINS WITH SPECIFIC BINDING PROPERTIES

TECHNICAL FIELD

The present invention relates to novel beta-sheet proteins with new or altered specific binding properties or a new or altered catalytic activity or new or altered fluorescence properties and also to methods for preparing proteins modified in such a way.

BACKGROUND ART

Antibodies and derivatives thereof are used in many areas of human and veterinary therapy, diagnostics and monitoring. One problem of utilizing the naturally occurring antibodies is the preparation thereof. The antibodies are still produced in an animal cell culture system, which is a very costly method. In some applications such as, for example, preparation of fusion proteins or a therapeutic use which requires rapid blood clearance and good tissue penetration, the size of naturally occurring antibody molecules represents another problem (Colcher et al., 1998). Recombinant antibody molecules such as scFvs (Bird et al., 1988), Miniantibodies (Pack and Plückthun, 1992) or bispecific antibodies (Holliger and Winter, 1993) are mainly composed of just the antigen-binding domains of the antibodies (VH and VL). Owing to their considerably reduced size, they show improved tissue penetration and are also better suited for fusions with other proteins than complete antibodies. Compared with the latter, though, recombinant antibody fragments are often more unstable, have low affinities and are difficult to prepare in recombinant form, owing to the disulphide bridges to be formed. Methods for stabilization and improved affinity of the recombinant antibody fragments include, inter alia testing various linker peptides and introduction of disulphide linkages (Glockshuber et al., 1990, Cumber et al., 1992, Brinkmann, 1997).

The sequence and length of the linker peptides can influence both the stability against proteases and the affinity of the antibody fragments (Pantoliano et al., 1991). The introduction of additional disulphide linkages into the conserved framework regions of the variable domains can lead to increased resistance to heat (Young et al., 1995) and denaturing agents and to increased yields in heterologous expression. In general, however, many scFvs show low stability and tend to aggregate already at 37° C. The instability may also be caused by using the common Fv-fragment cloning primers which can introduce new destabilizing mutations. The antibody fragments are produced in the bacterial system mainly by exporting into the periplasmic space, and optimizations regarding the redox state and simultaneous expression of foldings helpers are possible here, too.

SUMMARY OF THE INVENTION

It is an object of the present invention to provide novel proteins having new or altered binding properties, for example antibody-like properties, but, at the same time, do not display the above-described disadvantages of complete or recombinant antibody molecules.

It is a further object of the present invention to provide proteins which display new or altered enzymic or catalytic properties.

It is another object of the present invention to generate methods for forming the abovementioned proteins.

The objects mentioned above are achieved by a protein having the features characterized in claim 1. A method for preparing the proteins of the invention ensues from claim 21. Preferred embodiments of the invention ensue from the subclaims and the description below.

Alteration of the surface of a beta-sheet protein generates novel binding properties previously not present in the protein. These binding properties are generated by mutagenesis of a beta-sheet region. In spite of the de novo binding properties, the novel beta-sheet proteins are similar to the starting proteins with respect to structure and stability. Starting proteins for designing the novel binding molecules are proteins with a predominant beta-sheet structure such as, for example, gamma-crystalline, a structural protein of the eye lens. Based on the crystal structure, regions and amino acids in the beta-sheet of the starting proteins, which are exposed on the surface and thus accessible to the solvent or possible binding partners, are selected, for example, by means of computer analyses. Using genetic engineering methods, these regions or amino acid positions are mutagenized in the gene coding for the starting protein. Thus, a multiplicity of mutated genes (bank or library) coding for the different beta-sheet proteins mutants are prepared at the DNA level. Mutants having novel, desired binding properties are isolated with the aid of a suitable selection system such as, for example, the phage display system. In phage display, all protein mutants produced are exposed on the surface of bacteriophages (phage display library). These recombinant phages are studied with respect to their binding to the desired target molecules. Phages which expose on their surface beta-sheet mutants with specific binding to the target molecule are concentrated by repeated screening and isolated. Genes coding for binding beta-sheet mutants are obtained from the phages and expressed in a suitable expression system such as, for example, E. coli. Using the method described, it is surprisingly possible to prepare specifically binding proteins from beta-sheet proteins having no specific binding properties whatsoever, and mutants having the desired specificity are isolated from the library by applying a suitable screening method. Depending on the properties of the starting proteins, the beta-sheet mutants produced using the system described have advantages regarding size, stability and functionally active production in the heterologous, preferably bacterial, system, compared with, for example, antibodies and recombinant antibody fragments. These improved properties of the novel beta-sheet mutants make it possible to replace, for example, antibodies, recombinant antibody fragments of catalytic antibodies and to open up completely new application areas.

For example, the problems with antibodies, as illustrated above, can be solved according to the invention by designing proteins which have in each case specific binding properties and high stability against low pH, denaturing agents and elevated temperature, i.e. which withstand conditions under which antibodies are unstable. Generating proteins with beta-sheet structure and antibody-like binding properties, however, is only one possible field of application of the present invention. Further possible applications are opened up, for example, by generating beta-sheet proteins with new catalytic properties, for example resistance properties and fluorescent properties. An example of a protein whose fluorescent properties can be altered is GFP. The small proteins which are by nature highly stable are particularly suitable for the designing. Alteration of their surface generated, according to the invention and by way of example, new specific binding properties in the protein, with stability being retained.

A possible class of stable proteins, which was selected according to the invention and by way of example, is the crystallines. Crystallines which are the structural proteins of the eye lens are usually not subjected to cellular turnover and, consequently, have also extraordinary stability properties (Mandal et al., 1987, Rudolph et al., 1990). Gamma-crystallines, a class of crystallines in vertebrates, are monomeric proteins with a molecular mass of approximately 22 kDa. The main structural motif of the gamma-crystallines is the antiparallel beta-sheet (Hazes and Hol, 1992, Richardson et al., 1992, Hemmingsen et al., 1994). Gamma-crystallines consist of two very similar globular domains, an N- and a C-terminal domain, which are linked to one another by a V-shaped linker peptide. The folding pattern characteristic for gamma-crystallines ("greek-key" motif Slingsby, 1985, Wistow and Piatigorsky, 1988) is the most likely reason for the considerable thermostability and stability against denaturing agents (Mandal et al., 1987). Gamma-II-crystalline from calf eyes is a 21 kDa protein with, for its size, unusually many (7) cysteines which are in the reduced state under physiological conditions.

In its properly folded state, gamma-II-crystalline has no binding properties whatsoever. The inventive alteration (mutagenesis) of a selected solvent-exposed region of this protein, which consists of the beta-sheet structural motif, surprisingly resulted in alteration of the surface structure and charge pattern of the protein and thus in generation of new binding properties. In this connection, only regions or amino acid positions whose involvement in preserving the structure of the protein is insignificant were reacted. Mutagenesis of small beta-sheet proteins (Riddle et al., 1997) has shown that a high percentage of the protein is capable of forming the native beta-sheet structure correctly, despite considerable changes in the sequence.

Attempts at mutating particular protein regions with the aim of isolating molecules having improved or new binding properties exist already for recombinant antibody fragments (Nissim et al., 1994, de Kruif et al., 1995), for proteins with established binding properties (receptors, inhibitor proteins, DNA-binding proteins) and for peptide libraries (Cortese et al., 1995, Haaparanta and Huse 1995, McConell et al., 1996). In the case of antibodies, only the antigen-binding domains which are present as loop regions are mutagenized. This is likewise the case for most other proteins such as, for example, tendamistat (McConell and Hoess, 1995) or cytochrome $b_{562}$ (Ku and Schultz, 1995). Here too, loop regions are mutagenized. Examples of mutageneses in alpha-helices are the Z-domain of protein A (Nord et al., 1997) and the zinc-finger domain CP-1 (Choo and Klug, 1995). The previous mutageneses merely altered the specificity of the binding and always started from proteins with already established binding properties. A protein without binding properties was never used, nor was a beta-sheet structural motif specifically altered. In the method described here, for the first time a specific mutagenesis was carried out in the rigid beta-sheet region of a protein without any binding properties. This resulted, unexpectedly, in a protein with considerable stability and specific binding properties, comparable to antibody molecules.

A suitable system for isolating mutagenized beta-sheet proteins with de novo binding properties is the phage display system. This system makes possible very efficient screening of a large repertoire of protein variants for specific binding properties (Smith, 1985). In this connection, a protein variant is in each case presented on the surface of a filamentous phage and can interact with the target molecules immobilized on a solid phase. Proteins binding to the target molecule can be obtained by eluting the phages. After isolating the phage DNA, the DNA sequence of the specifically binding protein variants can be determined. In addition to the phage display system, it is also possible to apply other selection systems such as, for example, bacterial surface display (Stahl and Uhlen, 1997) or ribosome display (Hanes et al., 1997).

Using the above-described invention, it is surprisingly possible to alter, for example, the very stable beta-sheet protein gamma-II-crystalline by targeted, site-specific mutagenesis in the beta-sheet on the surface such that a protein with specific binding properties is generated from the non-binding protein. Randomizing eight amino acid positions thus leads, for the first time, to mutagenesis in a scaffolding molecule within a relatively rigid region of the protein. Thus a protein species which is "antibody-like" with respect to its specific binding properties is prepared from the beta-sheet protein gamma-II-crystalline. Gamma-II-crystalline or other small stable beta-sheet proteins can generally be used in the described method as novel scaffolding molecules for designing novel binding properties. The modelled beta-sheet proteins can replace, for example, recombinant antibodies in various applications. Due to their relatively small size (20 kDa), they are suited as fusion partners for other functional proteins (preparation of multifunctional proteins). Further possible uses are in gene therapy in which they can be employed as modules for cell-specific targeting of gene-therapy vectors and in intracellular immunization. Furthermore, beta-sheet mutants with catalytic properties can be used in enzyme application areas. The stability of the novel binding proteins makes additionally possible applications which cannot be carried out at present using recombinant antibodies, for example in human and veterinary medical diagnostics and therapy and in biosensor and bioseparation methods. Further fields of application are generally the pharmaceutical and cosmetic industries and the analysis and removal of harmful substances.

In the following, some preferred embodiments of the invention are described.

The proteins with beta-sheet structure, selected for mutagenesis according to the invention, have either no binding properties or no catalytic or enzymic activity or fluorescence properties or their activity, fluorescence properties or binding properties are such that an alteration, in particular improvement, is desirable.

Proteins with beta-sheet structure are known. An example of a protein class with beta-sheet is the crystallines, in particular alpha- beta- and gamma-crystallines. It is in principle possible to use crystallines from all kinds of animals, for example from vertebrates, rodents, birds and fish. Further examples of proteins which have beta-sheet structure and can be mutagenized according to the invention are: spherulins, heat shock proteins, cold shock proteins, beta-helix proteins, lipocalins, certins or transcription factors, fibronectins, GFP, NGF, tendamistat or lysozyme. For example, individual subunits or domains of the said proteins, for example crystallines, which have beta-sheet structure, are mutagenized according to the invention.

Among the crystallines, particular preferred mention must be made of gamma-crystalline for which it was possible, according to the invention and by way of example, to demonstrate that the beta-sheet structure thereof can be modified, i.e. mutagenized, such that new specific binding properties or new catalytic activities which are comparable to, for example, an antibody molecule are formed. An example of a gamma-crystalline is gamma-II-crystalline.

Examples of beta-helix proteins can be found, inter alia, in Jenkins J. et al., J. Struct. Biol. 1998, 122 (1-2): 236-46, Pickersgill, R. et al., J. Biol. Chem. 1998, 273 (38), 24600-4 and Raetz C. R. et al., Science 1995, 270 (5238), 997-1000.

The beta-sheet structure is defined by being essentially sheet-like and almost completely flat. In contrast to alpha-helices which are formed by a continuous part of the polypeptide chain, beta-sheets may be composed of various regions of the polypeptide chain. This makes it possible for regions which are relatively far apart in the primary structure to be located right next to one another. A beta-strand is typically 5-10 amino acids in length and is almost completely flat. The beta-strands are so close to one another that hydrogen bonds form between the C=O group of one and the NH group of the other strand and vice versa. Beta-sheets may be composed of a plurality of strands and have a sheet-like structure. The C-alpha atom is located alternately above or below the sheet-like plane. The amino acid side chains follow this pattern and are thus orientated alternately upwards and downwards. Depending on the orientation of the beta-strands, a distinction is made between parallel and antiparallel sheets. According to the invention, both can be mutagenized and used for preparing the claimed proteins.

For mutagenesis of the beta-sheet structure, those beta-sheet regions in the protein, which are close to the surface, are selected. An amino acid exposed on the surface can be identified on the basis of the available X-ray crystal structure. If no crystal structure is available, it is possible by means of computer analysis to try to predict beta-sheet regions exposed on the surface and accessibility of individual amino acid positions on the basis of the available primary structure (www.embl-heidelberg.de/predictprotein/predictprotein.html) or to model the 3D protein structure (www.expasy.ch/swissmo/SWISS-MODEL.html) and thus to obtain information about amino acids possibly exposed on the surface.

However, beta-sheet mutageneses for which a time-consuming preselection of the amino acid positions to be mutagenized can be dispensed with are also possible. Those DNA regions which code for the beta-sheet structures are isolated from their DNA environment, subjected to a random mutagenesis and subsequently re-integrated into the DNA coding for the protein, from which they have been removed previously. This is followed by a selection method for mutants having the desired binding properties and/or catalytic properties and/or fluorescence properties.

In another embodiment of the invention, the beta-sheet regions close to the surface are, as already described above, selected and the amino acid positions to be mutagenized are identified within these selected regions. These amino acid positions selected in this way can then be mutagenized at the DNA level either targeted, i.e. a codon coding for a particular amino acid is replaced by a codon coding for a different, previously selected specific amino acid, or this exchange is carried out within the framework of a random mutagenesis, with the amino acid position to be exchanged being defined but not the codon coding for the new, hitherto undefined amino acid.

Amino acids exposed on the surface are accessible to the surrounding solvent. If the accessibility of amino acids in a protein is more than 8% compared with the accessibility of the amino acid in the model tripeptide Gly-X-Gly, these amino acids are called amino acids exposed on the surface. These protein regions or individual amino acid positions are also preferred binding sites for possible binding partners which are to be selected for according to the invention. The binding partners may be, for example, antigens or substrates or substrate-transition-state analogues.

According to the invention, it is possible to mutagenize virtually all proteins which display beta-sheet structures located on the surface and accessible to a solvent or a binding partner. To this end, suitable proteins are mainly those which are particularly stable, i.e. resistant to denaturation, for example, or sufficiently "small".

"Mutagenization" means according to the invention the alteration of one or more amino acids exposed on the surface in the polypeptide chain with beta-sheet structure. This includes, for example, amino acid substitutions in which an amino acid with particular properties with respect to its polarity, charge, solubility, hydrophobicity or hydrophilicity is replaced by an amino acid with a different property, thus for example a non-polar, hydrophobic amino acid by a polar amino acid, a negatively charged amino acid by a positively charged amino acid, etc. The term "mutagenization" also comprises insertions and deletions of one more amino acids. A precondition is that the mutations comprise amino acids exposed on the surface in at least two beta-strands exposed on the surface of at least one beta-sheet exposed on the surface. The mutations are preferably and specifically introduced at individual amino acid positions in the beta-sheet or in selected regions of the beta-sheet. Mutagenizations may be present in one region or in a plurality of regions of the beta-sheet structure. The alterations may comprise adjacent amino acids or amino acids which are relatively far apart in the beta-sheet. The alterations may also comprise amino acids in various beta-sheets, i.e. in more than one beta-sheet. The insertions, deletions or substitutions of one or more amino acids are located in at least two beta strands exposed on the surface of at least one beta-sheet exposed on the surface. In this connection, it is possible to substitute, delete or insert one or more amino acids in one beta strand exposed on the surface, i.e. one beta strand exposed on the surface can have a plurality of mutations, if at least two beta strands exposed on the surface are mutated. In a further embodiment, in each case one beta-strand exposed on the surface of at least two beta-sheets exposed on the surface is mutagenized, i.e. one beta-sheet exposed on the surface has in each case at least one mutagenized beta-strand exposed on the surface. In another embodiment of the invention, the mutagenized beta-sheets exposed on the surface are arranged antiparallel to one another, and preference is given to at least two antiparallel arranged beta-sheets.

According to the invention, it is preferred, for example, that two or there beta-strands exposed on the surface are mutagenized. According to the invention, it is also possible that four or more beta-strands exposed on the surface are mutagenized. Furthermore, it is possible that at least two beta-strands in at least two beta-sheets are mutagenized, with preference being given to mutagenesis of three beta-strands in two antiparallel beta-sheets.

In one embodiment of the invention, mutagenesis is carried out by assembling DNA oligonucleotides having the amino acid codon NNK. It is, of course, also possible to use other codons (triplets).

The mutations are carried out such that the beta-sheet structure is retained. In general, mutagenesis takes place on the outside of a stable beta-sheet region exposed on the surface of the protein. It comprises both site-specific and random mutagenizations. Site-specific mutageneses which comprise a relatively small region in the primary structure (approx. 3-5 amino acids) can be carried out using the commercially available kits from Stratagene (QuickChange) or Bio-Rad (Muta-Gene phagemid in vitro mutagenesis kit) (cf. U.S. Pat. No. 5,789,166; U.S. Pat. No. 4,873,192).

If larger regions undergo site-specific mutagenesis, a DNA cassette has to be prepared, and the region to be mutagenized is obtained by assembling oligonucleotides containing the mutated and the unaltered positions (Nord et al., 1997; McConell and Hoess, 1995). Random mutageneses can be introduced by propagating the DNA in mutator strains or by PCR amplification (error-prone-PCR) (e.g. Pannekoek et al., 1993). In this case, a polymerase with increased error rate is used. In order to increase the extent of the introduced mutagenesis or to combine different mutations, it is possible to combine the mutations in the PCR fragments by means of DNA shuffling (Stemmer, 1994). The review by Kuchner and Arnold (1997) provides an overview of these mutagenesis strategies for enzymes. In order to carry out the said random mutagenesis in a selected DNA region, a DNA cassette which is utilized for the mutagenesis has to be constructed here, too.

The DNA molecules obtained in the mutagenesis step are expressed in a suitable expression system. Preference is given to those expression systems which facilitate subsequent selection and isolation of mutants having the desired binding properties and/or the desired catalytic or enzymic activity. Such expression vectors and expression systems are known to the skilled worker and have been described already in more detail above. Of course, it is also possible to use other expression systems which allow inventive selection for mutants with specific properties or activities.

Preference is given to using for expression and selection the phage display system in which all mutants produced at the DNA level are cloned into a phagemid and expressed on phage surfaces. In the case of proteins containing reduced cysteines, it is possible, in a particularly preferred embodiment of the invention, to add GSH, in order to improve exposition and selection of the mutants.

The invention includes the mutagenized proteins, DNA molecules, RNA molecules derived thereof and functional parts thereof which code for a protein which has a mutagenized beta-sheet structure and is capable of binding to a desired binding partner in a new or altered manner or which can have a new or altered catalytic activity for a substrate or new or altered fluorescence properties. The term "functional parts" relates to subunits, domains and epitopes of the protein with beta-sheet structure, which have been mutagenized according to the invention and possess the desired binding properties and activities or are partly responsible therefor.

Mutants having the desired binding properties and/or the desired catalytic activities and/or fluorescence properties are selected and isolated in a manner known per se. Examples of selection methods and isolation methods for mutants having new or altered binding properties and new or altered catalytic activities are described below:

When selecting for desired binding properties, the mutated proteins or functional parts thereof are contacted with their binding partners. Suitable detection methods select mutants having the desired binding properties.

When selecting for catalytic activity, the mutated proteins or functional parts thereof are connected with the substrates and then selected for the desired enzymic activity by suitable detection methods.

Catalytic Activity can be Selected for in Several Ways:

1. Phage Display:

Coupling of transition-state analogues to a solid phase and selecting the mutant library for the said analogues. These substances are analogues to transitional states of the substrate, which typically form during enzymic conversion of a substrate to the product (substrate-transition-state product). For this, however, the transition state of the substrate must be known. It is also possible to carry out a screening for substrate binding.

2. Without Phage Display:

Cloning of the mutants into a bacterial expression system and plating of the recombinant bacteria for forming individual colonies. The mutated protein can be expressed in the bacteria by adding inducers (e.g. IPTG) to the nutrient medium. The nutrient medium must furthermore contain the substrate whose conversion is to be screened for. The substrate must form an identifiable, e.g. coloured, product during conversion. Those bacteria which express a mutant converting the substrate in the nutrient medium require a different colour. An example would be the screening for beta-galactosidase activity and conversion of X-Gal (blue staining) (Zhang et al., 1997).

3. The Skilled Worker Knows Further Detection Methods:

Apart from the colour formation variant, it would also be possible, to select, for example, protein mutants which mediate a new resistance (addition of antibiotics to the nutrient medium) or which make possible growth on minimal nutrient media on which the "normal" bacterium will not grow. It is possible here to make use of the selective growth advantage of the bacteria having the new protein mutant (Crameri et al., 1997).

4. Expression and Secretion of the Mutated Proteins:

For example in bacteria, obtaining the supernatant and testing for the desired enzymic activity to be selected (You and Arnold, 1996). The present invention thus solves the problem of generating proteins having new binding properties or new catalytic properties by mutagenizing proteins with beta-sheet structures in this structural motif. Those proteins are selected for, which possess the desired new or altered, preferably improved binding properties or the desired new or altered, preferably improved, enzymic or catalytic activities. The system of the invention even makes it possible to alter beta-sheet proteins which have no binding properties or no enzymic properties such that, after mutagenization in the beta-sheet, they acquire binding properties or catalytic properties.

According to the invention, "binding properties" means, for example, the specific affinity of an antigen for an antibody. After the mutagenesis has been carried out according to the invention, the beta-sheet protein thus possesses antibody-like properties and combines the advantages of the high binding specificity of an antibody with the advantageous stability properties of a beta-sheet protein. The beta-sheet proteins with antibody-like properties, prepared according to the invention, may also possess a catalytic function.

However, the solution proposal according to the invention makes it also possible to generate proteins with beta-sheet structure, which have new or altered catalytic activities. The alteration of other protein properties, for example the fluorescent properties of GFP, would also be possible.

According to the invention, alteration of the binding properties, the catalytic activity or the fluorescence properties means both a deterioration and an improvement in the said properties, with an improvement being preferred.

According to the invention, a "protein having a new specific property" or "having a new catalytic activity" means a protein which previously has not had any specific binding property or catalytic activity and now has a specific binding property or a catalytic activity or a combination of both, due to the specific mutagenization of amino acids exposed on the surface in at least two beta-strands exposed on the surface of at least one beta-sheet exposed on the surface. However, this also includes proteins which already had a specific binding property or a catalytic activity prior to mutagenization and, after mutagenization in the beta-sheet, possess another, additional specific binding property and/or catalytic activity. It is, of course, also possible that a protein with a specific binding property now has a catalytic activity or vice versa.

The invention furthermore comprises those proteins which already possess a specific binding property and/or an enzymic or catalytic activity and/or fluorescence properties and which, after mutagenization of amino acids exposed on the surface in at least two beta-strands exposed on the surface of one or more beta-sheets exposed on the surface, obtain an improvement in, or, in more general terms, and alteration of their specific binding properties and/or their catalytic activity and/ or their fluorescence properties.

In this respect, the method of the invention and the proteins prepared thereby also differ from proteins and methods from the prior art, in which the beta-sheet structure was altered by random mutagenizations which were not directed towards the beta-sheet structure but towards the entire protein and which were in particular not targeted towards amino acids exposed on the surface in at least two beta-strands exposed on the surface of at least one beta-sheet exposed on the surface or which related to such amino acids exposed on the surface.

In a preferred embodiment of the invention, which will be described by way of example below, gamma-crystalline, as in the example of a protein with beta-sheet structure, was chosen as starting point for the mutagenesis. To this end, first amino acid positions exposed on the surface were selected through structural studies and mutagenized by mutagenization methods known per se. The mutants obtained were expressed in a suitable, likewise known expression system. The selection was directed towards those mutants whose amino acids exposed on the surface in the beta-sheet of the gamma-crystalline showed specific binding towards the antigen BSA-estradiol 17-hemisuccinate. Although a plurality of mutants having the desired binding property were isolated, only one carries the expected amino acid exchanges. Thus, an antibody-like non-immunoglobulin molecule was obtained, which is based on the starting protein gamma-crystalline.

The method of the invention makes it possible to prepare an indeed enormous number of mutants. Mutagenesis of just eight amino acid positions makes it possible to form $2.6 \times 10^{10}$ different protein species which can be analysed for the desired binding properties and catalytic activities.

According to the invention, it was furthermore shown that the fluorescence properties of a protein with beta-sheet structure can be altered by mutagenesis of amino acids exposed on the surface.

The mutated genes obtained can be propagated in suitable systems and the proteins can be expressed. Suitable expression systems are prokaryotic or eukaryotic systems. The DNA coding for the mutated protein is transferred, for example, into a suitable vector, for example into an expression vector, and introduced into a host cell by transformation, transfection or infection. The linkage to regulatory sequences which specifically control expression of the heterologous mutated DNA is advantageous, of course.

A host cell which may be used is a host cell of a higher eukaryote, for example a mammalian cell, or of a lower eukaryote, for example a yeast cell, or a prokaryotic cell, for example a bacterial cell. An example of a possible bacterial host cell is *E. coli* or *B. subtilis*. Cell-free translation systems for preparing the proteins by using RNA which is derived from the DNA of the present invention are also possible. Suitable cloning and expression systems are described in various textbooks for molecular biology, biotechnology and gene technology. Examples include Sambrook et al., 1989 and Ausubel et al., 1994.

BRIEF DESCRIPTION OF THE DRAWINGS

The invention, described in general terms above, is illustrated in more detail below on the basis of an exemplary embodiment and the attached drawings. The example is to be understood as a possible form of the invention and the invention is not restricted to this particular embodiment.

The attached figures show:

FIG. 1: Oligonucleotides for assembling the gamma-crystalline mutants, which include CDLIE1B (SEQ ID NO: 1), GCLIE2P (SEQ ID NO: 11), GCLI3P (SEQ ID NO: 12), GCLIB4P (SEQ ID NO: 13), GCLI5P (SEQ ID NO: 14), GCLI6P (SEQ ID NO: 15), GCLIB7P (SEQ ID NO: 16), GCLI8P (SEQ ID NO: 17), GCLIE9P (SEQ ID NO: 18), GCLIE10 (SEQ ID NO: 2), and GCLIA11B (SEQ ID NO: 3).

FIG. 2: Schematic representation of oligonucleotide assembling and subsequent PCR on streptavidin-loaded magnetic beads (MB). The positions marked with X indicate the randomized amino acid positions.

FIG. 7: Partial DNA sequence of the BSA-estradiol-17-hemisuccinate-binding gamma-II-crystalline mutant 12A (Mu 12A; SEQ ID NO: 9) in phagemid pGCKT 8-3 and of gamma-II-crystalline wild-type (WT; SEQ ID NO: 10) in pCANTAB 5E respectively. The introduced cleavage sites Sfi I (5') and Bst EII (3') are indicated by italics and underlining. The codons of the randomized amino acid positions are in bold type.

FIG. 8: Derived amino acid sequences of the BSA-estradiol-17-hemisuccinate-binding gamma-II-crystalline mutant 12A (Mu 12A; SEQ ID NO: 19) and of gamma-II-crystalline wild-type (WT; SEQ ID NO: 20) after expression in the phagemids and removal of the signal peptide. The randomized amino acid positions are indicated by bold type and amino acids which have actually been exchanged are indicated by bold type and are underlined. Amino acids additionally introduced at the N-terminals via the Sfi I cleavage site and the C-terminal E-tag fusion are shown in italics and underlined.

FIG. 9: Sequences of the primers used for cloning Mu 12A and gamma-II-crystalline into vector pET-20b, which include primers GC 20bbackWT (SEQ ID NO: 23), GC 20bback12A (SEQ ID NO: 24), and GC for 20b (SEQ ID NO: 25).

FIG. 10: Derived protein sequence of the BSA-estradiol-17-binding mutant 12A (SEQ ID NO: 21) and of bovine gamma-II-crystalline (SEQ ID NO: 22) after expression in pET-20b. The randomized amino acid positions are indicated by bold type and amino acids which have actually been exchanged are indicated by bold type and are underlined.

C-terminal amino acids additionally introduced via the cloning, including the 6 histidine are shown in italics and underlined.

FIG. 11: Concentration-dependent binding of mutant 12A (SEQ ID NO: 21) to the BSA-beta-estradiol-17-hemisuccinate conjugate. The binding of the mutant (12A SEQ ID NO: 21) and of gamma-II-crystalline (WT; SEQ ID NO: 22) to the conjugate (BSA-Estr. 17) and, as a control, to BSA was analysed.

FIG. 12: Stability of mutant 12A against the denaturing agent guanidine. The figure shows the emission maxima after incubating the purified mutant 12A (SEQ ID NO: 21) and gamma-II-crystalline (SEQ ID NO: 22) proteins with various concentrations of guanidine for various periods.

Figure 13A:
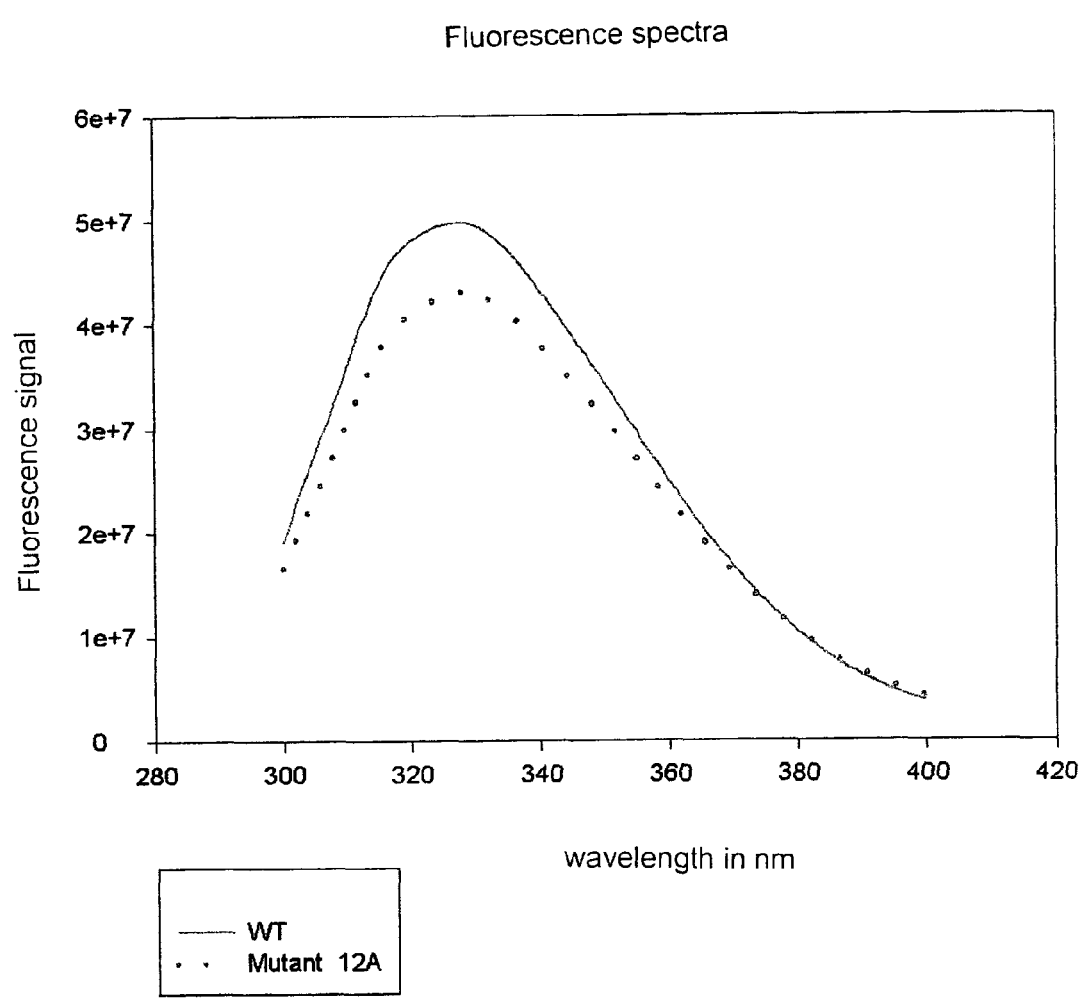
Figure 13B:
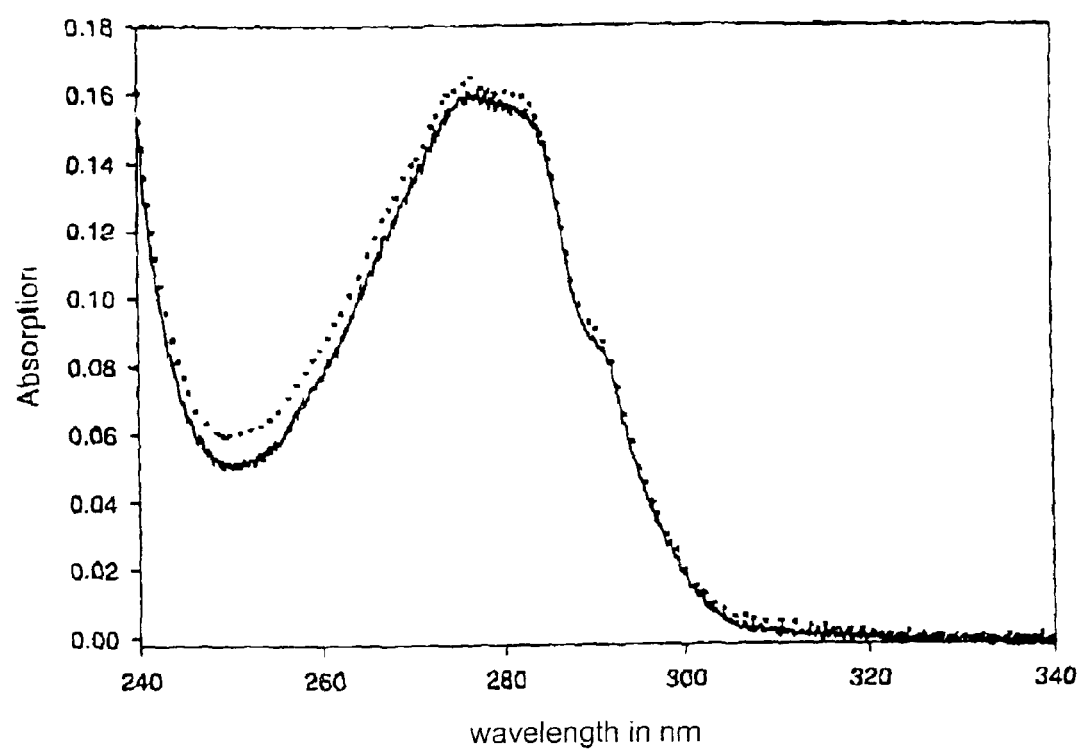

FIG. 13: Fluorescence emission spectrum of wild-type gamma-crystalline (SEQ ID NO: 22) and mutant 12A (SEQ ID NO: 21) in 50 mM Na phosphate, pH 6.5. The fluorescence signal (FIG. 13A) was measured at an excitation wavelength of 280 nm. The protein concentration was 100 µg/ml. FIG. 13B shows the absorbence spectra of the protein samples used for fluorescence measurement. The absorbence was determined in a cuvette with 1 cm path length.

DETAILED DESCRIPTION OF THE INVENTION

Example

Preparation of a Gamma-Crystalline Mutant with Specific Binding to the Hormone Estradiol The design of novel beta-sheet proteins with antigen-binding properties is shown on the basis of isolating a mutant of the bovine gamma-B-crystalline (gamma-II), which binds specifically to the hormone estradiol. Specific alteration of selected amino acid positions of a beta-sheet exposed on the surface produced a novel stable protein with beta-sheet structure and specific binding properties. After selecting the beta-sheet region or amino acids suitable for mutagenesis, a site-specific mutagenesis was carried out at the DNA level, and in a phagemid a beta-sheet mutant library was prepared, which makes expression and subsequent selection for novel binding properties of the mutants in the phage display system possible. The isolated mutant (SEQ ID NO: 19) was compared to the starting protein gamma-II-crystalline (SEQ ID NO: 20) with respect to its new properties.

Selection of a Suitable Region for Mutagenesis in Gamma-Crystalline

Based on the X-ray structure of gamma-II-crystalline (Wistow et al., 1983), the N-terminal domain of gamma-II-crystalline (GENBANK® Accession No. M16894) was selected for mutagenesis. Eight amino acids in all, which form a continuous surface segment, were identified there. The selected amino acids are part of a beta-sheet and should not contribute substantially to preserving the structure. They are amino acid positions which are accessible to the solvent and thus also to possible binding partners. The eight amino acids Lys 3, Thr 5, Tyr 7, Cys 16, Glu 18, Ser 20, Arg 37, and Asp 39 of SEQ ID NO: 22 comprise an area of approx. 6.1% of the total surface area of the protein.

Preparation of a DNA Pool of Mutated Gamma-II-Crystalline Genes

The eight amino acid positions were randomized by site-specific mutagenesis. This makes it possible to produce $2.6 \times 10^{10}$ different protein species. The region to be mutagenized was obtained at the DNA level by assembling individual oligonucleotides. This was followed by cloning into a phagemid constructed for selection in the phage display system.

Oligoassembling

For mutagenesis, 227 bp containing the 5' region of the gamma-crystalline mutants with the eight randomized amino acid positions and also suitable restriction cleavage sites were assembled on a solid phase. 10 individual oligonucleotides in all were used therefor, three of which contained the randomized amino acid positions (FIG. 1). During primer synthesis, the nucleotide mixture NN(T/G) was used at the eight positions to be mutagenized, resulting theoretically in 32 different codons at one position (cf. Nord et al., 1997). At the start of the assembling, biotinylated oligonucleotides were attached to streptavidin-loaded magnetic beads (MBs) from Dynal (M-280). After several attachment, ligation and polymeration steps, it was possible to amplify the pool of mutagenized regions of gamma-crystalline, assembled on the solid phase, by PCR (FIG. 2). The PCR products of approx. 250 bp in length contained an Sfi I cleavage site 5' and a Bst E11 cleavage site 3'.

All oligonucleotides used for assembling were adjusted to a concentration of 100 pmol/µl. First, the primers GCLIE1B (SEQ ID NO: 1) and GCLIE2P (SEQ ID NO: 11) were assembled. For this, 36 µl of washing and binding buffer (WB buffer: 1 M NaCl, 10 mM Tris-HCl pH 7.5, 1 mM EDTA) were added to in each case 4 µl of the primers and the mixture was incubated at 70° C. for 5 min. After assembly of the two primers and further incubation at 70° C. for 5 minutes, the primer mixture was slowly cooled to room temperature. 4 µl of the GCLIE1B/GCLIE2P primer hybrids were mixed with 56 µl of WB buffer and added to 300 µg of the streptavidin-loaded MBs which had been washed beforehand with washing and binding buffer. Incubation at room temperature for 15 minutes was followed by washing the MBs with WB buffer and TE buffer (10 mM Tris-HCl pH 7.5, 1 mM EDTA). A primer linker fragment is added to the MBs coupled to the first primer hybrid, which fragment is prepared as follows: 4 µl of primer GCLIB4P (SEQ ID NO: 13) or GCLI5P (SEQ ID NO: 14) are mixed with 36 µl of 1× ligation buffer from GIBCO BRL (50 mM Tris-HCl pH 7.6, 10 mM MgCl$_2$, 1 mM ATP, 1 mM DTT, 5% (w/v) polyethylene glycol-8000). After incubation at 70° C. for 5 minutes, both mixtures are combined, incubated at 70° C. for a further 5 min and cooled to room temperature. After adding 12 units of T4 DNA ligase (GIBCO BRL) and 8 µl of 1× ligation buffer, the reaction mixture is incubated at room temperature for 1 h. 12 µl of this GCLIE3P/GCLIB4P/GCLI5P bridging fragment are admixed with 54 µl of 1× ligation buffer and 6 units of ligase, and the mixture is added to the washed MBs containing the first primer hybrid and incubated at room temperature for 1 h. After the ligation reaction, the MBs are washed twice with TE buffer and taken up in 64 µl of 1× ligation buffer containing 8 µl of ligase. 8 µl of the assembled primer mixture GCLI6P (SEQ ID NO: 15)/GCLIB7P (SEQ ID NO: 16), which primers have been assembled beforehand in analogy to those of GCLIB4P/GCLI5P, were then added to the MBs. The ligation was again carried out at room temperature for 1 h. After washing the MBs twice in TE buffer, 12 µl of the $2^{nd}$ bridging fragment GCLIB8P (SEQ ID NO: 17)/GCLIE9P (SEQ ID NO: 18)/GCLIE10 (SEQ ID NO: 2) are added and the mixture is ligated for 1 h. The $2^{nd}$ bridging fragment is prepared analogously to the first bridging fragment, GCLIE9P (SEQ ID NO: 18) and GCLIE10 (SEQ ID NO: 2) being assembled first and then ligated with GCLI8P in the second step. The MBs with the immobilized primers are then again washed with TE buffer. The subsequent DNA-polymerase and ligase reaction fills in the gaps in the second strand. The MBs are incubated at 37° C. for 30 min in the following buffer mixture: 52.5 µl of H$_2$O, 6 µl of buffer L from Boehringer (100 mM Tris-HCl pH 7.5, 100 mM MgCl$_2$, 10 mM dithioerythritol), 0.5 µl of dNTPs (25 mM of each dNTP) and 1 µl (2 units) of Klenow fragment (Boehringer). Washing the MBs twice with TE buffer is followed by the ligation reaction at room temperature for 1 h. A 100 µl mixture contains 10 units of ligase. After two washing steps with TE buffer, the DNA strand non-covalently bound to the MBs is removed by treatment with 40 µl of 0.1 M NaOH for 30 s, and the MBs are resuspended in 60 µl of TE. The PCR for amplifying the library is carried out using the MBs as template. The PCR reaction mixture (50 µl) is prepared as follows: 6 µl of MBs, 5 µl of 10×PCR reaction buffer from Stratagene (100 mM KCl, 100 mM (NH$_4$)$_2$SO$_4$, 200 mM Tris-HCl pH 8.75, 20 mM MgSO$_4$, 1% Triton X-100, 1 mg/ml BSA), 1 µl (2.5 units) of Pfu DNA polymerase (Stratagene), 0.5 µl of dNTPs (25 mM of each dNTP), 0.35 µl of GCLIE1B (SEQ ID NO: 1). 0.35 µl of GCLIA11B (SEQ ID NO: 3) and 36.8 µl of H$_2$O. The PCR was carried out in 35 cycles with primer annealing at 550 for 1 min, a polymerase reaction at 72° C. for 1.5 min, denaturation at 95° C. for 1 min and a final polymerase reaction at 72° C. for 5 min.

Preparation of Phagemid pGCKT 8-3

Figures 3, 4:
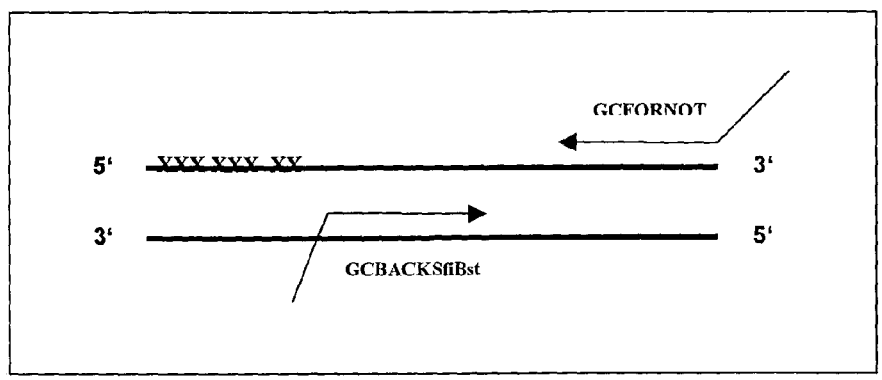
FIG. 3: Schematic representation of the amplification of the non-mutagenized region of gamma-II-crystalline.
FIG. 4: Oligonucleotides for amplifying the non-mutagenized region of gamma-II-crystalline, which include GCFORNOT (SEQ ID NO: 4) and GCBACKSfiBst (SEQ ID NO: 5).

Starting from phagemid pCANTAB 5E (PRAS kit from Pharmacia Biotech), a phagemid derivative for cloning the gamma-II-crystalline mutant band was thus constructed. The entire 3' region of gamma-II-crystalline (C-terminal domain: GENBANK Accession No. M16894) and the non-mutagenized 5' region were amplified by means of PCR using plasmid pGII (Mayr et al., 1994) as template and primers GCFORNOT (SEQ ID NO: 4) and GCBACKSfiBst (SEQ ID NO: 5: see FIGS. 3, 4).

The Sfi I (GCBACKSfiBst; SEQ ID NO: 5) and Not I (GCFORNOT; SEQ ID NO: 4) cleavage sites introduced by the primers make insertion of the PCR product into phagemid (GCFORNOT; SEQ ID NO: 4) PCANTAB 5E possible. Together with the GCBACKSfiBst (SEQ ID NO: 5) primer, a Bst EII cleavage site was additionally integrated into the gamma-crystalline gene, which allowed cloning of the mutated gamma-crystalline DNA fragments. de novo introduction of the cleavage site does not alter the amino acid sequence in gamma-II-crystalline. After sequencing, the PCR product was cloned as Sfi I/Not I fragment into phagemid Sfi I/Not I cut with PCANTAB 5E. The phagemid pGCKT8-3 constructed in this way was the starting point for preparing the gamma-II-crystalline phage display library.

Preparation of the Gamma-Crystalline Mutant-Library and Cloning of Wild-Type Gamma-II-Crystalline Phagemid pGCKT 8-3 was cut with Bst E11 and Sfi I restriction enzymes and subjected to phosphatase treatment (shrimps phosphatase from USB). After the individual cleavages, the DNA was fractionated by gel electrophoresis, and the cleaved vector fractions were excised and isolated from the agarose gels by means of electroelution. Any further enzymatic treatment was preceded by phenol/chloroform extraction and precipitation of the DNA with glycogen. The DNA fragment pool which had been amplified by means of PCR and which contained the mutated region of gamma-II-crystalline was cleaved with Sfi I and Bst EII restriction enzymes. A total 440 ng of phagemid and 110 mg of PCR product were used for ligating the PCR products into the prepared pGCKT 8-3 phagemid. The ligations were carried out with a total 44 units of T4 DNA ligase (GIBCO BRL) in 20 µl mixtures at 16° C. overnight. After inactivating the ligase at 70° C. for 20 minutes, the ligation reactions were desalted by drop dialysis for 1 h. In each case 30 µl of electrocompetent E. coli TG 1 cells were transformed with in each case 15 µl of the dialysed ligations. The electrocompetent cells were prepared and transformed as described in the PRAS-kit manual. The transformed cells were created onto glucose- and ampicillin-(100 µg/ml) containing SOBAG plates (see PRAS-kit manual from Pharmacia-Biotech) and incubated at 30° C. overnight. The GCUC-1 library prepared contained 250 000 original clones. The clones were washed off with 2×YT medium (see PRAS-kit manual) containing 1% glucose and 20% glycerol, aliquoted and stored at −80° C. The amplification factor of the library was determined to 7×10$^6$. The proportion of recombinant clones in the GCUC-1 library was 97%. Sequencing of randomly selected clones revealed that codons were used with the expected variants at the randomized amino acid positions. Expression rates of 30-60% were detected in the library by means of Western-blot analyses.

In control experiments, gamma-II-crystalline DNA was amplified using primers GCFORNOT (5' GAGTCATTCT-GCGGCCGCATAAAAATCCATCACCCGTCTTAAA GMCC 3'; SEQ ID NO: 4) and GCBACKSFI (5'CATGCCAT-GACTCGCGGCCC AGCCGGCCATGGGGAAGAT-CACTTTTTACGAGGAC 3'; SEQ ID NO: 6) and plasmid pGII (Mayr et al., 1994) as template. After cleavage with Not I and Sfi I restriction endonucleases, the sequenced PCR product was cloned into the Sfi I/Not I phagemid likewise cut with pCANTAB 5E.

A Phage Display Design and Selection for Novel Binding Properties

Figure 5:
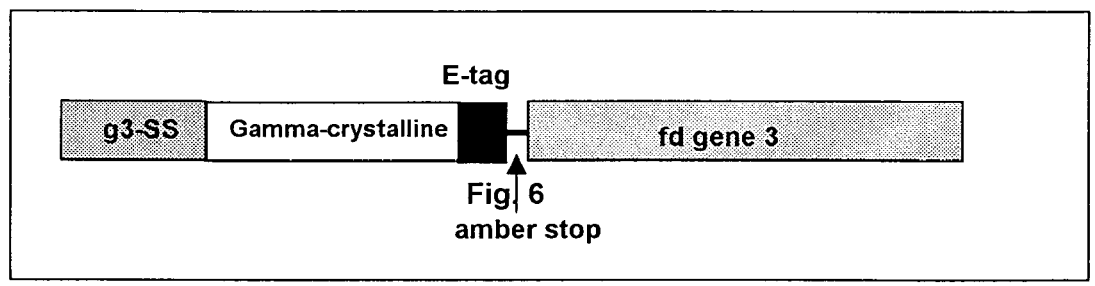
FIG. 5: Schematic representation of the pCANTAB 5E-gamma-II-crystalline expression cassette. g3-SS: signal peptide sequence of the phage protein G3; E-tag: 11 amino acids for immunological detection; fd Gen 3: minor coat protein 3 of the filamentous phage M13.

The commercially available phage display system PRAS from Pharmacia-Biotech was used for selecting gamma-crystalline mutants for binding properties. In the pCANTAB 5E (wild-type gamma-II-crystalline) and pGCKT 8-3 (gamma-crystalline mutants) phagemids used, the gamma-crystallines are fused N-terminally to the G3 signal peptide and C-terminally to an E-tag which makes immunological detection of the proteins possible (FIG. 5). Depending on the bacterial strain used, the amber stop codon after the E-tag is either recognized (E. coli HB 2151), and cleavage of the signal peptide is followed by secretion or overreading of the E. coli cell. After adding a helper phage, recombinant phages can be formed which expose the gamma-II-crystalline variants on their surface.

Optimization of Cultivation Conditions for the GCUC-1 Library and Gamma-II-Crystalline Wild-Type Phages Under the cultivation conditions described in the PRAS manual, it was not possible to detect in any of the recombinant phages the expected fusion proteins (gamma-II-crystalline/protein 3) by means of Westerb-blot analyses. Only the addition of reduced glutathione (GSG) during phage formation altered the redox state in the periplasm of the bacterial cell and thus provided more favourable conditions for phage assembling. When using the gamma-II-crystalline clone, it was possible to detect recombinant phages carrying the fusion protein only with the addition of GSH. Increasing GSH concentration also increased the proportion of gamma-II-crystalline phages. The optimal GSH concentration was determined to 8 mM. One reason for poor gamma-crystalline expression on the phage surface in the absence of GSH could be the high proportion of reduced cysteines (7) in gamma-crystalline. When the particularly unfolded gamma-crystalline enters the periplasm, it could, under the oxidative conditions prevailing there, misfold and form aggregates due to the formation of disulphide bridges. This could also suppress phage assembling. When using proteins with reduced cysteines in the phage display system, it may be possible to improve formation of recombinant phages generally by adding GSH.

Selection Process Using the GCUC1 Phage Display Library

To screen the GCUC-1 library, all glass equipment used was sterilized at 220° C. for 4 h and plastic material was sterilized with Helipur for 1 h. GCUC-1 library panning was carried out using BSA-beta-estradiol 17-hemisuccinate (Sigma) as antigen and microtitre plates (Maxisorp from NUNC) as solid phases. During the 3 rounds of panning, the stringency of the washing steps was increased. For the first cultivation, 100 ml of 2×YT medium containing 2% of glucose and ampicillin (100 µg/ml) were inoculated with 50 µl of the GCUC-1 library. The bacteria grew at 37° C. and 300 rpm to an $OD_{600}$ of 0.4. 800 µl of M13KO7 helper phage ($1 \times 10^{11}$ pfu/ml, GIBCO BRL) were added to 10 ml of this bacterial culture. This was followed by incubation at 37° C. for 30 min without and for a further 30 min with gentle agitation (50 rpm). The bacterial pellet was obtained by centrifugation at room temperature and 1500 rpm (Sorvall SS 34 Rotor) for 20 min and taken up in 100 ml of 2×YT medium containing 8 mM GSH, 100 µg/ml ampicillin and 50 µg/ml Kanamycin. The recombinant phages were produced by overnight culturing at 30° C. and 300 rpm. The supernatant containing the recombinant phages was obtained by two centrifugations at 10 800 g for in each case 15 minutes and subsequent filtration (pore size 0.45 µm). The phages were concentrated by adding 1/5 of PEG/NaCl solution (20% PEG-8000, 2.5 M NaCl) to the supernatant, incubating on ice for one hour and two centrifugations at 4° C. and 3 300 g for in each case 30 minutes. The phage pellet obtained was suspended in 4 ml of PBS pH 7.2, and remaining cell components were removed by centrifugation (10 min, 11 600 g, room temperature). For the selection process (panning), 1 ml of concentrated phages were mixed with 1 ml of a 6% strength BSA solution (6% BSA in PBS, pH 7.2) and incubated at room temperature for 10 min. In each case 100% of the phages treated in this way were added to the antigen-coated microtitre plate wells prepared as follows. NUNC-Maxisorp microtitre plates were coated with the antigen BSA-beta-estradiol 17-hemisuccinate. In each ases 100 µl of antigen solution (100 µg/ml in PBS pH 7.6) were introduced into 10 wells in total. The wells coated at room temperature overnight were washed three times with PBS, pH 7.6. Free binding sites were saturated by filling the wells with a 3% strength BSA/PBS solution, pH 7.2, at room temperature for 2 h. Prior to adding the BSA-treated phages, the wells were washed twice with a PBS solution (ph 7.2). Panning was carried out by agitating the microtitre plate gently (20 rpm) for 30 minutes followed by incubation without shaking at room temperature for 90 minutes. Unspecifically bound phages were removed by washing 10 times with PBS, pH 7.2/0.1% Tween-20 and washing 10 times with PBS, pH 7.2. Bound phages were eluted by adding in each case 100 µl of 100 mM triethylamine (freshly prepared) per well and incubating at room temperature for 10 minutes. The base-eluted phages (1 ml) were neutralized by adding 500 µl of 1 M Tris-HCl pH 7.4. 750 µl of these phages were used for infecting 9 ml of TG-1 cells cultivated on minimal medium plates and having an $OD_{600}$ of 0.4-0.5. For this, the bacteria were incubated with the phages at 37° C. for 30 min. It was possible to save phages which had bound particularly tightly and had not been removed from the microtitre plate by triethylamine treatment by direct infection of TG-1 cells. For this, in each case 100 µl of the cultivated TG-1 cells were added to the wells. After incubating at 37° C. for 30 minutes, the infected TG-1 cells were removed and combined with those from infection with the eluted phages. The infected bacteria were created onto 16×16 cm SOBAG plates and incubated at 30° C. overnight. In each case 1 µl of concentrated and eluted phages was used for determining the titre. The bacterial clones obtained were washed off the SOBAG plates with 12.5 ml of 2×YT, 20% glycerol. The second and third pannings were carried out similarly to the first with the following changes. Phage cultivation was repeated using 20 µL of the washed-off library in 20 ml of medium. 2 ml of the cultivated bacterial culture were used for infection with the helper phage (bacterial/phages weight ratio: 1/20). In the second panning the microtitre plates were washed first 15 times with PBS/Tween-20 and then 10 times with PBS and in the 3rd panning first 20 times with PBS/Tween-20 and then 10 times with PBS.

ELISA for Checking Concentration and Specific Binding

Figure 6:
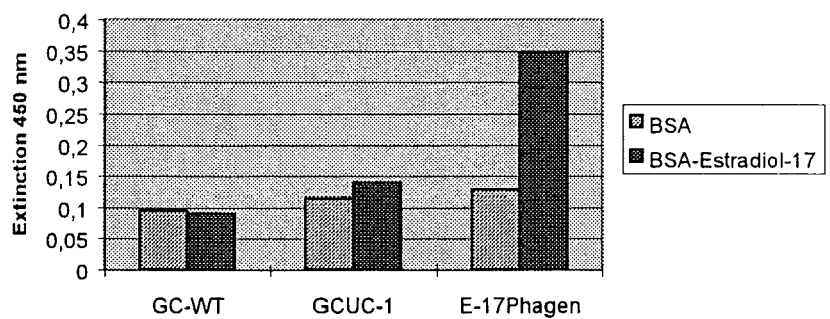
FIG. 6: Polyclonal phage ELISA with concentrated phages after 3$^{rd}$ panning. The microtitre plates were coated either with the BSA-beta-estradiol 17-hemisuccinate conjugate or just with BSA as control. Shown next to one another are the binding of gamma-II-crystalline wild-type phages (GC-WT), of the phages from the starting library (GCUC-1) and of the phages concentrated by repeated panning (E-17 phages) to the particular antigen.

Concentration of the phages specifically binding to the antigen was detected using a polyclonal phage ELISA. In addition to the eluted phages, phages of the staring library GCUC-1 and of wild-type gamma-II-crystalline were assayed for comparison. NUNC-Maxisorp plates were coated with 100 µl of BSA-estradiol17-hemisuccinate or BSA at a concentration of 2 µg/ml of PBS pH 7.6 at room temperature overnight. 3 washings of the wells with PBS, ph 7.6 were followed by blocking with 3% dried milk powder (Glücksklee)/PBS, pH 7.2 at 37° C. for 2 h and another (3) washings with PBS, pH 7.6. The non-concentrated recombinant phages isolated after phage cultivation were firstly blocked at room temperature for 1 h (1:1 mixture with 6% strength dried milk powder (Marvel)/PBS pH 7.6. 100 µl of the blocked phages were applied per well and incubated at 37° C. for 1 h. Washing the wells in each case 3 times with PBS/Tween-20 and PBS was followed by incubation with the anti-M13 antibody-POD conjugate (Pharmacia-Biotech, dilution 1:5 000 in 3% Glücksklee/PBS) at 37° C. for 1 h. After washing the plates, the enzyme-bound antibody was detected using 100 µl of Immuno-Pure-TMB substrate (Pierce). The colour reaction was stopped by adding 100 µl of 2M $H_2SO_4$ and extinction at 450 nm was determined. The result of the concentration of the phages binding to the BSA-estradiol conjugate, after the 3rd panning, is shown in FIG. 6.

Isolation and Characterization of Individual Phages with Specific Binding to the Conjugate 80 individual clones were selected from the bacterial clones obtained after the 3rd panning. Phages were isolated from the clones and assayed individually in the monoclonal phage ELISA with respect to their antigen binding. Individual bacterial clones were cultivated in 100 µl of 2×YT medium containing 2% glucose and 100 µg/ml ampicillin in polypropylene microtitre plates (NUNC) with gentle agitation (100 rpm) overnight. 2 µl of these bacterial cultures were diluted 1:100 in the same medium and cultured at 100 rpm at 37° C. to an $OD_{600}$ of 0.4. Phages were obtained as described for the selection process. Deep well polypropylene microtitre plates from TECAN were used for phage cultivation. For the ELISA, 200 µl of the phage supernatant obtained after centrifugation (not concentrated) were blocked with 40 µl of 6×PBS/18% at room temperature for 1 h. 30 out of 80 clones assayed showed significant binding of the recombinant phages to BSA-Estradiol-17 and not to BSA assayed in parallel. Phages with wild-type gamma-II-crystalline showed in a control experiment no binding to BSA-estradiol-17 whatsoever. 14 selected binding phages were sequenced using the IRD 800-labelled primers pCANR1LAB (5'CCATGAT-TACGCCAAGCTTTGGAGCC 3'; SEQ ID NO: 7) and GCLISEQ (5'CTGAAAGTGCCGGTGTGTTGC 3'; SEQ ID NO: 8). Only in one case, sequencing revealed a gamma-crystalline variant (Mu 12A) which was mutated exclusively in the eight randomized amino acid positions. A number of clones showed shifts in the reading frame and, although theoretically coding for a functional protein, had alterations which were not exclusively in the expected gamma-crystalline region. These frame shift mutants were not studied further.

Characterization of Beta-Sheet Mutant 12A

Expression of the fusion protein Mu 12A-minor coat protein 3 on the surface of the recombinant phages and expression of Mu 12A in *E. coli* strain HB 2151 were detected by means of Western-blot analyses using the anti-G3P and anti-E-Tag antibodies (Pharmacia-Biotech), respectively. The DNA sequences of mutant 12A (SEQ ID NO: 9) in phagemid pGCKT 8-3 and of gamma-II-crystalline wild-type (SEQ ID NO: 10) are depicted in FIG. 7. The DNA sequence starts at the Sfi I cleavage site which is already present in the starting phageimid pCANTAB 5E and ends, in the case of pGCKT 8-3, at the Bst E11 site newly introduced into the gamma-II-crystalline gene and, in the case of the gamma-II-crystalline wild-type gene, at the original sequence. FIG. 8 depicts the amino acid sequences derived therefrom. Codon randomization at amino acid position 36 does not change the amino acid arginine at this position. Computer modeling of mutant 12A (SEQ ID NO: 19) shows that the amino acid exchanges do not cause large alterations in the protein structure compared with the starting protein. However, the net charge becomes more positive.

Expression of Mu 12A in pET-20b

In order to characterize mutant 12A in detail, the DNA (SEQ ID NO: 9) was recloned into plasmid pET-20b (Novagen). The plasmid makes possible a high expression of the recombinant DNA in *E. coli* strain BL 21 and simple purification of the foreign proteins. Genes are expressed here without signal peptide and with a C-terminal fusion of 6 histidine residues. The DNAs of mutant 12A (SEQ ID NO: 9) and of bovine gamma-II-crystalline wild-type (SEQ ID NO: 10) were amplified by means of PCR using the appropriate phagemid DNA and primers GC 20bback12A/GC (SEQ ID NO: 24) for 20b for mutant 12A and GC 20bbackWT/GC (SEQ ID NO: 23) for 20b for the wild-type (FIG. 9). The PCR fragments were cleaved with restriction endonucleases Nde I and Bam HI and cloned into vector pET20b cut with Nde I/Bam HI. FIG. 10 depicts the theoretical amino acid sequence of mutant 12 A (SEQ ID NO: 21) and of gamma-II-crystalline (SEQ ID NO: 22), respectively, after expression in pET-20b. The first 10 N-terminal amino acids of mutant 12 A (SEQ ID NO: 21) were confirmed by N-terminal protein sequencing.

Cultivation and Purification of Mutant and Wild-Type in pET-20b

In order to study the binding properties and stability of the mutant in detail, large amounts of mutant 12A and wild-type proteins were prepared. BL 21 cells were transformed with plasmids pET-20b/Mu 12A and pET-20b/Gamma-II-crystalline, respectively. The clones were cultivated by diluting a preculture 1:100 with LB medium/100 µg/ml ampicillin and agitating the culture at 200 rpm and 37° C. up to an $OD_{600}$ of 0.5. Expression of the gamma-crystalline was induced by adding IPTG (final concentration 1 mM). Culturing was continued overnight at 30° C. and 200 rpm. The bacteria cells were harvested by centrifugation at 4° C., 6 000 rpm (Sorvall GS3 rotor) for 10 min. The cell pellet was suspended in 30 ml of 2×PBS with addition of 150 µl of 200 mM PMSF and 10 µl of DNAse (Boehringer). The cells were then disrupted twice using a Gaulin press at 800-1000 PSIG. The supernatant containing the soluble proteins was obtained after centrifugation of the cell suspension at 4° C. and 20 000 rpm (Sorvall SS 34 rotor) for 1 h. The gamma-crystallines fused to 6 histidine residues were purified by affinity chromatography at 4° C. 8 ml of Ni-NTA were equilibrated with 50 ml of 2×PBS/10 mM imidazole. The supernatant containing the soluble proteins was then slowly agitated with the equilibrated column material in a bach process on a roller shaker overnight. Introducing the suspension into a chromatography column was followed by washing with 2×PBS/10 mM imidazole/300 mM NaCl. The bound protein was eluted with 2×PBS/250 mM imidazole. DTT (final concentration 10 mM) was added to the eluted proteins. This was followed by 2 dialysis steps at 4° C. for in each case 8 h: 1st with 100 mM Na phosphate buffer pH 6.0/1 mM EDTA/1 mM DTT and 2nd with 10 mM Na phosphate buffer pH 6.0/1 mM EDTA. The supernatant obtained after a final centrifugation (4° C., 30 min, 20 000 rpm in Sorvall SS 34 rotor) contained the purified protein (Mu 12A or Gamma-II-crystalline) which was used for binding studies and stability studies.

Specific binding of mutant 12A to the BSA-estradiol-17-hemisuccinate conjugate was assayed by carrying out an ELISA, with increasing concentrations of purified mutant 12A-His-Tag protein being used. Increasing amounts of gamma-II-crystalline wild-type (likewise with His-Tag) were used as control, and binding of both purified proteins to BSA was assayed. The concentration-dependant ELISA was carried out using NUNC-Tm plates. Antigen coating with the BSA-estradiol-17-hemisuccinate conjugate or with BSA was carried out at room temperature overnight. Coating was carried out with in each case 100 µl of antigen at a concentration of 20 µg/ml of PBS pH 7.6. After washing (2×PBS pH 7.6) and blocking the plates (3% Marvel/PBS at 37° C. for 2 h), in each case 1-13 µl of the protein stock solution (concentration 0.63 mg/ml) of purified Mu 12A or gamma-II-crystalline were introduced into a total 100 µl of reaction solution (PBS, 3% Marvel, x µl of protein) and incubated in the wells at 37° C. for 2 h. The secondary antibodies used were the tetra-His antibody from Qiagen in a dilution of 1:3000 and the anti-mouse POD antibody (Sigma) in a dilution of 1:2000. The antibodies were diluted with a 3% strength Marvel/PBS solution and 100 µl were added to the wells and incubated at 37° C. for in each case 1 h. The substrate reaction was carried out as described for the polyclonal phage ELISA. The result of this ELISA in FIG. 11 shows clearly that increasing extinctions are measured only with increasing concentrations of mutant 12A. No increase was detected using gamma-II-crystalline. Likewise, no reaction with BSA was observed. This shows specific binding of mutant 12A compared with the starting protein.

Stability was studied by recording guanidine denaturation because of mutant 12A and of gamma-II-crystalline. For this purpose, the purified proteins were incubated at a final concentration of 20 µg/ml with increasing concentrations of guanidinium at 20° C. for one and three days. In total 15 guanidinium concentrations were adjusted in a range from 0-5.5 M in a 1 mM DTT/0.1 M Na phosphate buffer pH 6.0 solution. After one and three days, respectively, a 300-400 nm fluorescence emission spectrum of each mixture was recorded. The excitation wavelength was 280 nm. FIG. 12 depicts the emission maxima determined as a function of guanidinium concentrations. The stability of gamma-II-crystalline is higher than that of mutant 12A both after one day and after three days. However, compared with antibody molecules, the stability of mutant 12A is much higher.

Change in Fluorescence Properties of Mutant 12A

Fluorescence spectra were recorded in order to test whether the fluorescence properties of mutant 12A have changed compared with wild-type protein. For this purpose, in each case 100 µg/ml of wild-type protein or mutant 12A (in 50 mM Na phosphate, pH 6.0) were excited at 280 nm and fluorescence was measured in a wavelength range from 300 to 400 nm in a cuvette of 1 cm pathlength. The slit width was 5 nm both for excitation and for emission.

The detected fluorescence signal had a maximum of 329 nm both for wild-type and for mutant 12A. However, the fluorescence intensity of mutant 12A, with only 86% signal intensity, was distinctly lower compared with gamma-crystalline wild-type (100%) (see FIG. 13A).

Mutant 12A and wild-type have an identical total number of fluorophores. However, sequence alterations in the mutant (Y→K at Position 8 and C→Y at Position 15) cause a change in the fluorescence signal. The difference in fluorescence intensity can be attributed to the fact that the tyrosine residues in positions 8 and 15, respectively, have different fluorescence properties.

REFERENCES

Bird, R. E., Hardman, K. D., Jacobson, J. W., Johnson, S., Kaufman, B. M., Lee, S.-M., Lee, T., Pope, H. S., Riordan, G. S, and Whitlow, M. (1988): Single-chain antigen-binding proteins. Science 242, 423-426.

Brinkmann, U., di Carlo A., Vasmatzis, G., Kurochkina, N., Beers, R., Byungkook, L. and Pastan, I. (1997): Stabilization of a recombinant Fv fragment by base-loop interconnection and VH-VL permutation. J. Mol. Biol. 268, 107-117.

Choo, Y. and Klug, A. (1995): Designing DNA-binding proteins on the surface of filamentous phage. Curr. Opin. Biotechnol. 6, 431-436.

Colcher, D., Pavlinkova, G., Beresford, G., Booth, B. J., Choudhury, A. and Batra, S. K. (1998): Pharmacokinetics and biodistribution of genetically-engineered antibodies. Q. J. Nucl. Med. 42, 225-241.

Cortese R., Monaci, P., Luzzago, A., Santini, C., Bartoli, F., Cortese, I., Fortugno, P., Galfre, G., Nicosia, A. and Felici, F. (1995): Selection of biologically active peptides by phage display of random peptide libraries. Curr. Opin. Biotechnol. 6, 73-80.

Cumber, J. A., Ward, E. S., Winter, G., Parnell, G. D. and Wawrzynczak, E. J. (1992): Comparative stabilities in vitro and in vivo of a recombinant mouse antibody FvCys fragment and a bisFvCys conjugate. J. of Immunology 149, 120-126.

Glockshuber, R., Malia, M., Pfitzinger I. and Plückthun, A. (1990): A comparison of strategies to stabilize immunoglobulin Fv-fragments. Biochemistry 29, 1362-1367.

Haaparanta T. and Huse W. D. (1995): A combinatorial method for constructing libraries of long peptides displayed by filamentous phage. Mol. Diversity. 1, 39-52.

Hanes, J. et al. (1997): In vitro selection and evolution of functional proteins by using ribosome display. Proc. Natl. Acad. Sci. USA. 94, 4937-42.

Hazes, B. and Hol, W. G. J. (1992): Comparison of the hemocyanin β-barrel with other greek key β-barrels: possible importance of the "β-zipper" in protein structure and folding. Proteins: Struct., Funct. Gen. 12, 278-298.

Hemmirigsen, J. M., Gernert, K. M., Richardson, J. S. and Richardson, D.C. (1994): The tyrosine corner: a feature of most greek key β-barrel proteins. Prot. Science 3, 1927-1937.

Holliger, H. and Winter G. (1993): Engineering bispecific antibodies. Curr. Opin. Biotech. 4, 446-449.

de Kruif, J., Boel, E. and Logtenberg, T. (1995): Selection and application of human single chain Fv antibody fragments from a semi-synthetic phage antibody display library with designed CDR3 regions. J. Mol. Biol. 248, 97-105.

Ku, J. and Schultz, P. G. (1995): Alternate protein frameworks for molecular recognition. Proc. Natl. Acad. Sci. USA 92, 6552-6556.

Mayr, E.-M., Jaenicke, R. and Glockshuber, R. (1994): Domain interactions and connecting peptides in lens crystallins. J. Mol. Biol. 235, 84-88.

Mandal, K., Chakrabart, B., Thomson, J. and Siezen, R. J. (1987): Structure and stability of β-crystallins. Denaturation and proteolysis behaviour. J. Biol. Chem. 262, 8096-8102.

McConell S. and Hoess R. H. (1995): Tendamistat as a scaffold for conformationally constrained phage peptide libraries. J. Mol. Biol. 250, 460-470.

McConell, S. J., Uveges, A. J., Fowlkes, D. M. and Spinella, D. G (1996): Construction and screening of M13 phage libraries displaying long random peptides. Mol. Diversity 1, 165-176.

Nissim, A., Hoogenboom, H. R., Tomlinson, I. M., Flynn, G., Midgley, C., Lane, D. and Winter, G. (1994): Antibody fragments from a 'single pot' phage display library as immunochemical reagents. EMBO J. 13, 692-698.

Nord K., Gunneriusson, E., Ringdahl, J., Stahl, S., Uhlen, M. and Nygren, P. A. (1997): Binding proteins selected from combinatorial libraries of an β-helical bacterial receptor domain. Nat. Biotechnol. 8, 772-777.

Pack, P. and Plückthun, A. (1992): Miniantibodies: use of amphipathic helices to produce functional, flexibly linked dimeric Fv fragments with high avidity in Escherichia coli. Biochemistry 31, 1579-1584.

Pantoliano, M. W., Bird, R. E., Johnson, S., Asel, E. D., Dodd, S. W., Wood, J. F. and Hardman, K. D. (1991): Conformational stability, folding, and ligand-binding affinity of single-chain Fv immunoglobulin fragments expressed in Escherichia coli. Biochemistry 30, 10117-10125.

Richardson, J. S., Richardson, D. C., Tweedy, N. B., Gernert, K. M., Quinn, T. P., Hecht, M. H., Erickson, B. W., Yan, Y., McClain, R. D., Donlan, M. E. and Surles, M. C. (1992): Looking at proteins: representations, folding, packing and design. Biophys. J. 63, 1186-1209.

Riddle, D. S., Santiago, J. V., Bray-Hall, S. T., Doshi, N., Grantcharova, Q. Y and Baker, D. (1997): Functional rapidly folding proteins from simplified amino acid sequences. Nature structural biology 4, 805-809.

Rudolph, R., Siebendritt, R., Nesslauer, G., Sharma, A. and Jaenicke, R. (1990): Folding of an all-β protein: independent domain folding in GammaBII-crystallin from calf eye lens. Proc. Natl. Acad. Sci. USA 87, 4625-4629.

Slingsby, C. (1985): Structural variation in lens crystallins. TIBS10, 281-284.

Smith, G. P (1985): Filamentous Fusion Phage: Novel expression vectors that display cloned antigens on the virion surface. Science 228, 1315-1317.

Stahl, S, and Uhlen, M. (1997): Bacterial surface display: trends and progress. TIBTECH 15, 185-192.

Wistow, G. J. and Piatigorsky, J. (1988): Lens crystallins: the evolution and expression of proteins for a highly specialized tissue. Ann. Rev. Biochem. 57, 479-504.

Wistow, G. J., Turnell, B., Summers, L., Slingsby, C. Moss, D., Miller, L., Lindley, P. and Blundell, T. (1983): X-ray analysis of the eye lens protein y-II-crystallin at 1.9 A° resolution. J. Mol. Biol. 170, 175-202.

Young, N. M., MacKenzie, C. R., Narang, S. A., Oomen, R. P. and Baenziger, J. E. (1995): Thermal stabilization of a single-chain Fv antibody fragment by introduction of a disulphide bond. FEBS Lett. 377, 135-139.

Ausubel, F. M., Brent, R., Kinston, R. E., Moore, D. D., Seidmann, J. G., Smith, J. A. and Struhl, K. (1994): Current protocols in molecular biology. John Wiley & Sons, Inc.

Crameri, A., Dawes, G., Rodriguez, E., Jr., Silver, S. and Stemmer, W. P. (1997): Molecular evolution of an arsenate detoxification pathway by DNA shuffling. Nat. Biotechnol. 5, 436-438.

Kuchner, O. and Arnold, F. H. (1997): Directed evolution of enzyme catalysts. TIBTECH 15, 523-530.

Pannekoek, H., van Meijer M., Schleef, R. R., Loskutoff, d. J. and Barbas, C. F. (1993): Functional display of human plasminogen-activator inhibitor 1 (PAI-1) on phages: Novel perspectives for structure-function analysis by error-prone DNA synthesis. Gene 128, 135-140.

Sambrook, J., Maniatis, T. and Fritsch, E. F. (1989): Molecular Cloning: A laboratory manual. Cold spring Harbor. Cold Spring Harbour Laboratory Press, New York.

Stemmer, W. P. C. (1994): Rapid evolution of a protein in vitro by DNA shuffling. Nature 370, 389-391.

You, L. and Arnold, F. H. (1996): Directed evolution of subtilisin E in *Bacillus subtilis* to enhance total activity in aqueous dimethylformamide. Protein Eng. 1, 77-83.

Zhang, J. H., Dawas, G. and Stemmer, W-P. (1997): Directed evolution of a fucosidase from a galctosidase by DNA shuffling and screening. Proc. Natl. Acad. Sci. U.S.A. 94, 4504-4509.

What is claimed is:

1. A mutagenized bovine gamma-II-crystallin polypeptide with a new binding activity towards a binding partner, wherein amino acids on a surface of a bovine gamma-II-crystallin of SEQ ID NO: 22 is mutagenized, and further wherein:

the amino acids that are mutagenized are selected from the group consisting of Lys 3, Thr 5, Tyr 7, Cys 16, Glu 18, Ser 20, Arg 37, and Asp 39 of the bovine gamma-II-crystallin of SEQ ID NO: 22;

said beta-sheet, said beta-strands, and said amino acids are located on a surface of said gamma-crystallin polypeptide and are thus accessible to a solvent or a binding partner; and the mutagenizing is selected from the group consisting of an insertion, a deletion, a substitution, and combinations thereof, such that the mutagenized gamma-crystallin polypeptide has a new binding activity towards a binding partner, with the proviso that the gamma-crystallin polypeptide without substitution, deletion, insertion, or combinations thereof has no binding activity at the surface of the beta-sheet structure wherein the amino acids are mutagenized, and after substitution, deletion, insertion, or combinations thereof at the surface of the beta-sheet structure, the gamma-crystallin polypeptide has a new binding activity towards a binding partner.

2. The mutagenized bovine gamma-II-crystallin of claim 1, wherein the mutagenized bovine gamma-II-crystallin has a new antigen binding specificity for a compound selected from the group consisting of estradiol and BSA-β-estradiol-17-hemisuccinate, and further wherein the protein has an amino acid sequence comprising one of SEQ ID NO: 19 and SEQ ID NO: 21.

3. The mutagenized gamma-crystallin polypeptide of claim 1, wherein each amino acid substitution occurs at an amino acid selected from the group consisting of Lys 3, Thr 5, Tyr 7, Cys 16, Glu 18, Ser 20, Arg 37, and Asp 39 of the bovine gamma-II-crystallin of SEQ ID NO: 22.

4. The mutagenized gamma-crystallin polypeptide of claim 3, wherein the mutagenized gamma-crystallin polypeptide is present in a library of mutagenized gamma-crystallin polypeptides, and further wherein different members of the library comprise different amino acid substitutions at one or more amino acids selected from the group consisting of Lys 3, Thr 5, Tyr 7, Cys 16, Glu 18, Ser 20, Arg 37, and Asp 39 of the bovine gamma-II-crystallin of SEQ ID NO: 22.

5. The mutagenized gamma-crystallin polypeptide of claim 4, wherein the library is a phage display library and the mutagenized gamma-crystallin polypeptide is displayed on by the phage.

* * * * *

UNITED STATES PATENT AND TRADEMARK OFFICE
CERTIFICATE OF CORRECTION

PATENT NO.        : 7,601,803 B1                                   Page 1 of 1
APPLICATION NO. : 10/030605
DATED             : October 13, 2009
INVENTOR(S)       : Fiedler et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1184 days.

Signed and Sealed this

Fifth Day of October, 2010

David J. Kappos
*Director of the United States Patent and Trademark Office*

SEQUENCE LISTING

```
<160> NUMBER OF SEQ ID NOS: 25

<210> SEQ ID NO 1
<211> LENGTH: 45
<212> TYPE: DNA
<213> ORGANISM: Artificial Sequence
<220> FEATURE:
<223> OTHER INFORMATION: GCLIE1B primer designed according to mutant
      bovine gamma-II crystalline DNA sequence.  See Figure 1.
<220> FEATURE:
<221> NAME/KEY: misc_feature
<222> LOCATION: (1)..(45)
<223> OTHER INFORMATION: GCLIE1B primer designed according to mutant
      bovine gamma-II crystalline DNA sequence.  See Figure 1.

<400> SEQUENCE: 1
cgcgcgcgtc tcacaaagat acatgccatg actcgcggcc cagcc              45

<210> SEQ ID NO 2
<211> LENGTH: 50
<212> TYPE: DNA
<213> ORGANISM: Artificial Sequence
<220> FEATURE:
<223> OTHER INFORMATION: GCLIE10 primer designed according to mutant
      bovine gamma-II crystalline DNA sequence.  See Figure 1
<220> FEATURE:
<221> NAME/KEY: misc_feature
<222> LOCATION: (1)..(50)
<223> OTHER INFORMATION: GCLIE10 primer designed according to mutant
      bovine gamma-II crystalline DNA sequence.  See Figure 1.

<400> SEQUENCE: 2
gccgcaggaa gtactggtga ccctggtagt tggggcgctc atacagcatc         50

<210> SEQ ID NO 3
<211> LENGTH: 41
<212> TYPE: DNA
<213> ORGANISM: Artificial Sequence
<220> FEATURE:
<223> OTHER INFORMATION: GCLIA11B primer designed according to mutant
      bovine gamma-II crystalline DNA sequence.  See Figure 1
<220> FEATURE:
<221> NAME/KEY: misc_feature
<222> LOCATION: (1)..(41)
<223> OTHER INFORMATION: GCLIA11B primer designed according to mutant
      bovine gamma-II crystalline DNA sequence.  See Figure 1.

<400> SEQUENCE: 3
ccatcagccc catcagcgaa ctttgccgca ggaagtactg g                  41

<210> SEQ ID NO 4
<211> LENGTH: 48
<212> TYPE: DNA
<213> ORGANISM: Artificial Sequence
<220> FEATURE:
<223> OTHER INFORMATION: GCFORNOT primer for amplification of bovine
      gamma-II crystalline DNA in plasmid pGII.  See Figures 3 and 4
```

```
<220> FEATURE:
<221> NAME/KEY: misc_feature
<222> LOCATION: (1)..(48)
<223> OTHER INFORMATION: GCFORNOT primer for amplification of bovine
      gamma-II crystalline DNA in plasmid pGII.  See Figures 3 and 4

<400> SEQUENCE: 4
gagtcattct gcggccgcat aaaaatccat cacccgtctt aaagaacc            48

<210> SEQ ID NO 5
<211> LENGTH: 59
<212> TYPE: DNA
<213> ORGANISM: Artificial Sequence
<220> FEATURE:
<223> OTHER INFORMATION: GCBACKSfiBst primer for amplification of bovine
      gamma-II crystalline DNA in plasmid pGII.  See Figures 3 and 4
<220> FEATURE:
<221> NAME/KEY: misc_feature
<222> LOCATION: (1)..(59)
<223> OTHER INFORMATION: GCBACKSfiBst primer for amplification of bovine
      gamma-II crystalline DNA in plasmid pGII.  See Figures 3 and 4

<400> SEQUENCE: 5
gcggcccagc cggccgctgc tggatgctgt atgagcgccc caactaccag ggtcaccag   59

<210> SEQ ID NO 6
<211> LENGTH: 55
<212> TYPE: DNA
<213> ORGANISM: Artificial Sequence
<220> FEATURE:
<223> OTHER INFORMATION: GCBACKSfi primer for amplification of bovine
      gamma-II crystalline DNA in plasmid pGII
<220> FEATURE:
<221> NAME/KEY: misc_feature
<222> LOCATION: (1)..(55)
<223> OTHER INFORMATION: GCBACKSfi primer for amplification of bovine
      gamma-II crystalline DNA in plasmid pGII

<400> SEQUENCE: 6
catgccatga ctcgcggccc agccggccat ggggaagatc acttttacg aggac        55

<210> SEQ ID NO 7
<211> LENGTH: 26
<212> TYPE: DNA
<213> ORGANISM: Artificial Sequence
<220> FEATURE:
<223> OTHER INFORMATION: pCAR1LAB primer for DNA sequencing.
<220> FEATURE:
<221> NAME/KEY: misc_feature
<222> LOCATION: (1)..(26)
<223> OTHER INFORMATION: pCAR1LAB primer for DNA sequencing.

<400> SEQUENCE: 7
ccatgattac gccaagcttt ggagcc                                      26

<210> SEQ ID NO 8
<211> LENGTH: 21
<212> TYPE: DNA
<213> ORGANISM: Artificial Sequence
<220> FEATURE:
<223> OTHER INFORMATION: GCLISEQ primer for DNA sequencing.
<220> FEATURE:
<221> NAME/KEY: misc_feature
<222> LOCATION: (1)..(21)
<223> OTHER INFORMATION: GCLISEQ primer for DNA sequencing.

<400> SEQUENCE: 8
ctgaaagtgc cggtgtgttg c                                           21
```

<210> SEQ ID NO 9
<211> LENGTH: 176
<212> TYPE: DNA
<213> ORGANISM: Bos sp.

<400> SEQUENCE: 9
ggcccagccg gccatgggga ggatcaagtt taaagaggac cggggcttcc agggccacta    60
ttacagttgc aatagcgact gccccaacct gcagccctat ttcagccgct gtaactccat   120
cagggtgctg agcggctgct ggatgctgta tgagcgcccc aactaccagg gtcacc       176

<210> SEQ ID NO 10
<211> LENGTH: 176
<212> TYPE: DNA
<213> ORGANISM: Bos sp.

<400> SEQUENCE: 10
ggcccagccg gccatgggga agatcacttt ttacgaggac cggggcttcc agggccactg    60
ctacgagtgc agcagcgact gccccaacct gcagccctat ttcagccgct gtaactccat   120
ccgcgtggac agcggctgct ggatgctgta tgagcgcccc aactaccagg gccacc       176

<210> SEQ ID NO 11
<211> LENGTH: 55
<212> TYPE: DNA
<213> ORGANISM: Artificial Sequence
<220> FEATURE:
<223> OTHER INFORMATION: GCLIE2P primer designed according to mutant
      bovine gamma-II crystalline DNA sequence.  See Figure 1.
<220> FEATURE:
<221> NAME/KEY: misc_feature
<222> LOCATION: (1)..(55)
<223> OTHER INFORMATION: GCLIE2P primer designed according to mutant
      bovine gamma-II crystalline DNA sequence.  See Figure 1.

<400> SEQUENCE: 11
ccccatggcc ggctgggccg cgagtcatgg catgtatctt tgtgagacgc gcgcg          55

<210> SEQ ID NO 12
<211> LENGTH: 36
<212> TYPE: DNA
<213> ORGANISM: Artificial Sequence
<220> FEATURE:
<223> OTHER INFORMATION: GCLI3P primer designed according to mutant
      bovine gamma-II crystalline DNA sequence.  See Figure 1.
<220> FEATURE:
<221> NAME/KEY: misc_feature
<222> LOCATION: (1)..(36)
<223> OTHER INFORMATION: GCLI3P primer designed according to mutant
      bovine gamma-II crystalline DNA sequence.  See Figure 1
<220> FEATURE:
<221> NAME/KEY: misc_feature
<222> LOCATION: (1)..(36)
<223> OTHER INFORMATION: n is a, c, g, or t
<220> FEATURE:
<221> NAME/KEY: misc_feature
<222> LOCATION: (1)..(36)
<223> OTHER INFORMATION: k is g or t

<400> SEQUENCE: 12
ggccatgggg nnkatcnnkt ttnnkgagga ccgggg                               36

<210> SEQ ID NO 13
<211> LENGTH: 24
<212> TYPE: DNA
<213> ORGANISM: Artificial Sequence
<220> FEATURE:
<223> OTHER INFORMATION: GCLIB4P primer designed according to mutant
      bovine gamma-II crystalline DNA sequence.  See Figure 1.

```
<220> FEATURE:
<221> NAME/KEY: misc_feature
<222> LOCATION: (1)..(24)
<223> OTHER INFORMATION: GCLIB4P primer designed according to mutant
      bovine gamma-II crystalline DNA sequence. See Figure 1.

<400> SEQUENCE: 13
gtggccctgg aagccccggt cctc                                         24

<210> SEQ ID NO 14
<211> LENGTH: 44
<212> TYPE: DNA
<213> ORGANISM: Artificial Sequence
<220> FEATURE:
<223> OTHER INFORMATION: GCLI5P primer designed according to mutant
      bovine gamma-II crystalline DNA sequence. See Figure 1.
<220> FEATURE:
<221> NAME/KEY: misc_feature
<222> LOCATION: (1)..(44)
<223> OTHER INFORMATION: GCLI5P primer designed according to mutant
      bovine gamma-II crystalline DNA sequence. See Figure 1.
<220> FEATURE:
<221> NAME/KEY: misc_feature
<222> LOCATION: (1)..(44)
<223> OTHER INFORMATION: n is a, c, g, or t
<220> FEATURE:
<221> NAME/KEY: misc_feature
<222> LOCATION: (1)..(44)
<223> OTHER INFORMATION: k is g or t

<400> SEQUENCE: 14
cttccagggc cacnnktacn nktgcnnkag cgactgcccc aacc                   44

<210> SEQ ID NO 15
<211> LENGTH: 20
<212> TYPE: DNA
<213> ORGANISM: Artificial Sequence
<220> FEATURE:
<223> OTHER INFORMATION: GCLI6P primer designed according to mutant
      bovine gamma-II crystalline DNA sequence. See Figure 1.
<220> FEATURE:
<221> NAME/KEY: misc_feature
<222> LOCATION: (1)..(20)
<223> OTHER INFORMATION: GCLI6P primer designed according to mutant
      bovine gamma-II crystalline DNA sequence. See Figure 1.

<400> SEQUENCE: 15
tgcagcccta tttcagccgc                                              20

<210> SEQ ID NO 16
<211> LENGTH: 47
<212> TYPE: DNA
<213> ORGANISM: Artificial Sequence
<220> FEATURE:
<223> OTHER INFORMATION: GCLIB7P primer designed according to mutant
      bovine gamma-II crystalline DNA sequence. See Figure 1.
<220> FEATURE:
<221> NAME/KEY: misc_feature
<222> LOCATION: (1)..(47)
<223> OTHER INFORMATION: GCLIB7P primer designed according to mutant
      bovine gamma-II crystalline DNA sequence. See Figure 1.

<400> SEQUENCE: 16
gatggagtta cagcggctga aatagggctg caggttgggg cagtcgc                47

<210> SEQ ID NO 17
<211> LENGTH: 45
<212> TYPE: DNA
<213> ORGANISM: Artificial Sequence
<220> FEATURE:
<223> OTHER INFORMATION: GCLI8P primer designed according to mutant
``` bovine gamma-II crystalline DNA sequence.  See Figure 1.
<220> FEATURE:
<221> NAME/KEY: misc_feature
<222> LOCATION: (1)..(45)
<223> OTHER INFORMATION: GCLI8P primer designed according to mutant
      bovine gamma-II crystalline DNA sequence.  See Figure 1.
<220> FEATURE:
<221> NAME/KEY: misc_feature
<222> LOCATION: (1)..(45)
<223> OTHER INFORMATION: n is a, c, g, or t
<220> FEATURE:
<221> NAME/KEY: misc_feature
<222> LOCATION: (1)..(45)
<223> OTHER INFORMATION: k is g or t

<400> SEQUENCE: 17
tgtaactcca tcnnkgtgnn kagcggctgc tggatgctgt atgag         45

<210> SEQ ID NO 18
<211> LENGTH: 37
<212> TYPE: DNA
<213> ORGANISM: Artificial Sequence
<220> FEATURE:
<223> OTHER INFORMATION: GCLIE9P primer designed according to mutant
      bovine gamma-II crystalline DNA sequence.  See Figure 1.
<220> FEATURE:
<221> NAME/KEY: misc_feature
<222> LOCATION: (1)..(37)
<223> OTHER INFORMATION: GCLIE9P primer designed according to mutant
      bovine gamma-II crystalline DNA sequence.  See Figure 1.

<400> SEQUENCE: 18
cgccccaact accagggtca ccagtacttc ctgcggc             37

<210> SEQ ID NO 19
<211> LENGTH: 198
<212> TYPE: PRT
<213> ORGANISM: Bos sp.

<400> SEQUENCE: 19

Ala Ala Gln Pro Ala Met Gly Arg Ile Lys Phe Lys Glu Asp Arg Gly
1               5                   10                  15

Phe Gln Gly His Tyr Tyr Ser Cys Asn Ser Asp Cys Pro Asn Leu Gln
            20                  25                  30

Pro Tyr Phe Ser Arg Cys Asn Ser Ile Arg Val Leu Ser Gly Cys Trp
        35                  40                  45

Met Leu Tyr Glu Arg Pro Asn Tyr Gln Gly His Gln Tyr Phe Leu Arg
    50                  55                  60

Arg Gly Asp Tyr Pro Asp Tyr Gln Gln Trp Met Gly Phe Asn Asp Ser
65                  70                  75                  80

Ile Arg Ser Cys Arg Leu Ile Pro Gln His Thr Gly Thr Phe Arg Met
                85                  90                  95

Arg Ile Tyr Glu Arg Asp Asp Phe Arg Gly Gln Met Ser Glu Ile Thr
            100                 105                 110

Asp Asp Cys Pro Ser Leu Gln Asp Arg Phe His Leu Thr Glu Val His
        115                 120                 125

Ser Leu Asn Val Leu Glu Gly Ser Trp Val Leu Tyr Glu Met Pro Ser
    130                 135                 140

Tyr Arg Gly Arg Gln Tyr Leu Leu Arg Pro Gly Glu Tyr Arg Arg Tyr
145                 150                 155                 160

Leu Asp Trp Gly Ala Met Asn Ala Lys Val Gly Ser Leu Arg Arg Val
                165                 170                 175

Met Asp Phe Tyr Ala Ala Ala Gly Ala Pro Val Pro Tyr Pro Asp Pro

```
                180                 185                 190
Leu Glu Pro Arg Ala Ala
            195

<210> SEQ ID NO 20
<211> LENGTH: 198
<212> TYPE: PRT
<213> ORGANISM: Bos sp.

<400> SEQUENCE: 20

Ala Ala Gln Pro Ala Met Gly Lys Ile Thr Phe Tyr Glu Asp Arg Gly
1               5                   10                  15

Phe Gln Gly His Cys Tyr Glu Cys Ser Ser Asp Cys Pro Asn Leu Gln
            20                  25                  30

Pro Tyr Phe Ser Arg Cys Asn Ser Ile Arg Val Asp Ser Gly Cys Trp
        35                  40                  45

Met Leu Tyr Glu Arg Pro Asn Tyr Gln Gly His Gln Tyr Phe Leu Arg
50                  55                  60

Arg Gly Asp Tyr Pro Asp Tyr Gln Gln Trp Met Gly Phe Asn Asp Ser
65                  70                  75                  80

Ile Arg Ser Cys Arg Leu Ile Pro Gln His Thr Gly Thr Phe Arg Met
                85                  90                  95

Arg Ile Tyr Glu Arg Asp Asp Phe Arg Gly Gln Met Ser Glu Ile Thr
            100                 105                 110

Asp Asp Cys Pro Ser Leu Gln Asp Arg Phe His Leu Thr Glu Val His
        115                 120                 125

Ser Leu Asn Val Leu Glu Gly Ser Trp Val Leu Tyr Glu Met Pro Ser
130                 135                 140

Tyr Arg Gly Arg Gln Tyr Leu Leu Arg Pro Gly Glu Tyr Arg Arg Tyr
145                 150                 155                 160

Leu Asp Trp Gly Ala Met Asn Ala Lys Val Gly Ser Leu Arg Arg Val
                165                 170                 175

Met Asp Phe Tyr Ala Ala Ala Gly Ala Pro Val Pro Tyr Pro Asp Pro
            180                 185                 190

Leu Glu Pro Arg Ala Ala
            195

<210> SEQ ID NO 21
<211> LENGTH: 197
<212> TYPE: PRT
<213> ORGANISM: Bos sp.

<400> SEQUENCE: 21

Met Gly Arg Ile Lys Phe Lys Glu Asp Arg Gly Phe Gln Gly His Tyr
1               5                   10                  15

Tyr Ser Cys Asn Ser Asp Cys Pro Asn Leu Gln Pro Tyr Phe Ser Arg
            20                  25                  30

Cys Asn Ser Ile Arg Val Leu Ser Gly Cys Trp Met Leu Tyr Glu Arg
        35                  40                  45

Pro Asn Tyr Gln Gly His Gln Tyr Phe Leu Arg Arg Gly Asp Tyr Pro
50                  55                  60

Asp Tyr Gln Gln Trp Met Gly Phe Asn Asp Ser Ile Arg Ser Cys Arg
65                  70                  75                  80

Leu Ile Pro Gln His Thr Gly Thr Phe Arg Met Arg Ile Tyr Glu Arg
                85                  90                  95

Asp Asp Phe Arg Gly Gln Met Ser Glu Ile Thr Asp Asp Cys Pro Ser
```

-continued

```
                    100                 105                 110
Leu Gln Asp Arg Phe His Leu Thr Glu Val His Ser Leu Asn Val Leu
            115                 120                 125
Glu Gly Ser Trp Val Leu Tyr Glu Met Pro Ser Tyr Arg Gly Arg Gln
        130                 135                 140
Tyr Leu Leu Arg Pro Gly Glu Tyr Arg Arg Tyr Leu Asp Trp Gly Ala
145                 150                 155                 160
Met Asn Ala Lys Val Gly Ser Leu Arg Arg Val Met Asp Phe Tyr Ser
                165                 170                 175
Asp Pro Asn Ser Ser Val Asp Lys Leu Ala Ala Leu Glu His
            180                 185                 190
His His His His His
        195

<210> SEQ ID NO 22
<211> LENGTH: 197
<212> TYPE: PRT
<213> ORGANISM: Bos sp.

<400> SEQUENCE: 22

Met Gly Lys Ile Thr Phe Tyr Glu Asp Arg Gly Phe Gln Gly His Cys
1               5                   10                  15
Tyr Glu Cys Ser Ser Asp Cys Pro Asn Leu Gln Pro Tyr Phe Ser Arg
            20                  25                  30
Cys Asn Ser Ile Arg Val Asp Ser Gly Cys Trp Met Leu Tyr Glu Arg
        35                  40                  45
Pro Asn Tyr Gln Gly His Gln Tyr Phe Leu Arg Arg Gly Asp Tyr Pro
    50                  55                  60
Asp Tyr Gln Gln Trp Met Gly Phe Asn Asp Ser Ile Arg Ser Cys Arg
65                  70                  75                  80
Leu Ile Pro Gln His Thr Gly Thr Phe Arg Met Arg Ile Tyr Glu Arg
                85                  90                  95
Asp Asp Phe Arg Gly Gln Met Ser Glu Ile Thr Asp Asp Cys Pro Ser
            100                 105                 110
Leu Gln Asp Arg Phe His Leu Thr Glu Val His Ser Leu Asn Val Leu
        115                 120                 125
Glu Gly Ser Trp Val Leu Tyr Glu Met Pro Ser Tyr Arg Gly Arg Gln
    130                 135                 140
Tyr Leu Leu Arg Pro Gly Glu Tyr Arg Arg Tyr Leu Asp Trp Gly Ala
145                 150                 155                 160
Met Asn Ala Lys Val Gly Ser Leu Arg Arg Val Met Asp Phe Tyr Ser
                165                 170                 175
Asp Pro Asn Ser Ser Val Asp Lys Leu Ala Ala Leu Glu His
            180                 185                 190
His His His His His
        195

<210> SEQ ID NO 23
<211> LENGTH: 33
<212> TYPE: DNA
<213> ORGANISM: Artificial Sequence
<220> FEATURE:
<223> OTHER INFORMATION: GC20bbackWT primer for cloning bovine gamma-II
      crystalline DNA into vector pET-205.  See Figure 9
<220> FEATURE:
<221> NAME/KEY: misc_feature
<222> LOCATION: (1)..(33)
<223> OTHER INFORMATION: GC20bbackWT primer for cloning bovine gamma-II
```

-continued crystalline DNA into vector pET-205. See Figure 9

<400> SEQUENCE: 23
gggaattcca tatggggaag atcactttt acg                                33

<210> SEQ ID NO 24
<211> LENGTH: 33
<212> TYPE: DNA
<213> ORGANISM: Artificial Sequence
<220> FEATURE:
<223> OTHER INFORMATION: GC20bback12A primer for cloning Mu12A into
      vector pET-205. See Figure 9
<220> FEATURE:
<221> NAME/KEY: misc_feature
<222> LOCATION: (1)..(33)
<223> OTHER INFORMATION: GC20bback12A primer for cloning Mu12A into
      vector pET-205. See Figure 9

<400> SEQUENCE: 24
gggaattcca tatggggagg atcaagttta aag                               33

<210> SEQ ID NO 25
<211> LENGTH: 29
<212> TYPE: DNA
<213> ORGANISM: Artificial Sequence
<220> FEATURE:
<223> OTHER INFORMATION: GCfor20b primer for cloning Mu12A and bovine
      gamma-II crystalline DNA into vector pET-205. See Figure 9
<220> FEATURE:
<221> NAME/KEY: misc_feature
<222> LOCATION: (1)..(29)
<223> OTHER INFORMATION: GCfor20b primer for cloning Mu12A and bovine
      gamma-II crystalline DNA into vector pET-205. See Figure 9

<400> SEQUENCE: 25
cgcggatccg aataaaaatc catcacccg                                    29